(12) United States Patent
Panitch et al.

(10) Patent No.: US 10,828,370 B2
(45) Date of Patent: Nov. 10, 2020

(54) SELECTIN AND ICAM/VCAM PEPTIDE LIGAND CONJUGATES

(71) Applicant: Purdue Research Foundation, West Lafayette, IN (US)

(72) Inventors: Alyssa Panitch, Davis, CA (US); Rebecca Scott, West Lafayette, IN (US); Kinam Park, West Lafayette, IN (US); James Wodicka, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 215 days.

(21) Appl. No.: 15/310,416

(22) PCT Filed: May 12, 2015

(86) PCT No.: PCT/US2015/030424
§ 371 (c)(1),
(2) Date: Nov. 10, 2016

(87) PCT Pub. No.: WO2015/175565
PCT Pub. Date: Nov. 19, 2015

(65) Prior Publication Data
US 2018/0326077 A1 Nov. 15, 2018

Related U.S. Application Data

(60) Provisional application No. 61/992,056, filed on May 12, 2014.

(51) Int. Cl.
| | | |
|---|---|---|
| *A61K 38/08* | (2019.01) | |
| *A61K 47/42* | (2017.01) | |
| *C07D 487/04* | (2006.01) | |
| *C08B 37/02* | (2006.01) | |
| *C08B 37/00* | (2006.01) | |
| *C08B 37/08* | (2006.01) | |
| *A61K 47/61* | (2017.01) | |
| *A61K 47/54* | (2017.01) | |
| *A61P 9/10* | (2006.01) | |
| *A61P 29/00* | (2006.01) | |
| *A61P 9/14* | (2006.01) | |
| *C07K 14/47* | (2006.01) | |

(52) U.S. Cl.
CPC ............ *A61K 47/42* (2013.01); *A61K 47/545* (2017.08); *A61K 47/61* (2017.08); *A61P 9/10* (2018.01); *A61P 9/14* (2018.01); *A61P 29/00* (2018.01); *C07D 487/04* (2013.01); *C07K 14/4725* (2013.01); *C08B 37/0021* (2013.01); *C08B 37/0069* (2013.01); *C08B 37/0072* (2013.01)

(58) Field of Classification Search
None
See application file for complete search history.

(56) References Cited

U.S. PATENT DOCUMENTS

| | | |
|---|---|---|
| 5,648,458 A | 7/1997 | Cwirla et al. |
| 6,451,969 B1 | 9/2002 | Fukuda et al. |
| 8,188,218 B2 | 5/2012 | Siahaan et al. |
| 8,846,003 B2 | 9/2014 | Panitch et al. |
| 9,173,919 B2 | 11/2015 | Paderi et al. |
| 9,200,039 B2 | 12/2015 | Panitch et al. |
| 9,217,016 B2 | 12/2015 | Panitch et al. |
| 9,512,192 B2 | 12/2016 | Panitch et al. |
| 2005/0191344 A1 | 9/2005 | Zalipsky et al. |
| 2006/0241022 A1* | 10/2006 | Bowen ............ C07K 7/06 424/133.1 |
| 2010/0196284 A1 | 8/2010 | Lindner et al. |
| 2012/0276137 A1 | 11/2012 | Freese et al. |
| 2016/0129076 A1 | 5/2016 | Panitch et al. |
| 2017/0043023 A1 | 2/2017 | Panitch et al. |
| 2017/0275345 A1 | 9/2017 | Panitch et al. |
| 2018/0030091 A1 | 2/2018 | Paderi et al. |
| 2019/0022175 A1 | 1/2019 | Panitch et al. |
| 2019/0330276 A1 | 10/2019 | Panitch et al. |

FOREIGN PATENT DOCUMENTS

| | | | |
|---|---|---|---|
| WO | WO-2004/045542 | 6/2004 | |
| WO | WO-2004045542 A2 * | 6/2004 | ........... A61K 38/178 |
| WO | WO-2009/120995 | 10/2009 | |
| WO | WO-2010/129547 | 11/2010 | |
| WO | WO-2010129547 A1 * | 11/2010 | ........... A61K 31/726 |
| WO | WO-2011/163492 | 12/2011 | |
| WO | WO-2012/112767 | 8/2012 | |
| WO | WO-2012/162534 | 11/2012 | |
| WO | WO-2014/144969 | 9/2014 | |
| WO | WO-2015/164822 | 10/2015 | |
| WO | WO-2016/061147 | 4/2016 | |
| WO | WO-2016/168743 | 10/2016 | |

(Continued)

OTHER PUBLICATIONS

Chittasupho et al., Hyaluronic acid graft polymers displaying peptide antigen modulate dendritic cell response in vitro, Molecular Pharmaceutics, 2014 (published online Dec. 4, 2013); 11(1), pp. 367-373.
Extended European Search Report for European Patent Application No. 15792627.0 dated Apr. 19, 2018. (8 pages).
International Preliminary Report on Patentability for International Application No. PCT/US2015/030424 dated Nov. 15, 2016. (10 pages).
International Search Report and Written Opinion for PCT/US2015/030424 dated Sep. 16, 2015, 13 pages.
Feng et al., Peptides Derived from the Complementarity-determining Regions of Anti-Mac-1 Antibodies Block Intercellular Adhesion Molecule-1 Interaction with Mac-1*, The Journal of Biological Chemistry 1998, vol. 273, No. 10, pp. 5625-5630.

(Continued)

*Primary Examiner* — Satyanarayana R Gudibande
(74) *Attorney, Agent, or Firm* — Sheppard Mullin Richter & Hampton LLP

(57) ABSTRACT

The invention relates to peptide conjugates that can bind to endothelial cells, and that are useful for reducing the incidence and severity of endothelial dysfunction in mammals.

26 Claims, 4 Drawing Sheets

Specification includes a Sequence Listing.

(56) References Cited

FOREIGN PATENT DOCUMENTS

| WO | WO-2016161333 | 10/2016 |
| WO | WO-2019/010484 | 1/2019 |
| WO | WO-2019/010485 | 1/2019 |
| WO | WO-2019/010490 | 1/2019 |

OTHER PUBLICATIONS

Fukuda et al., A Peptide Mimic of E-Selectin Ligand Inhibits Sialyl Lewis X-dependent Lung Colonization of Tumor Cells1, Cancer Research 2000, 60, pp. 450-456.

Kalstad et al., Inhibition of Icam-Mediated Monocyte Adhesion with a Bioresponsive Dextran-Based Conjugate, Proceedings of the Second Joint EMBS/BMES Conference 2002, pp. 736-737.

Kawai et al., High frequency of phylogenetically diverse reductive dehalogenase-homologous genes in deep subseafloor sedimentary metagenomes, Frontiers in Microbiology 2014, vol. 5, Article 80. (15 pages).

Martens et al., Peptides Which Bind to E-selectin and Block Neutrophil Adhesion*, the Journal of Biological Chemistry 1995, vol. 270, No. 36, pp. 21129-21136.

Yusuf-Makagiansar et al., Sequence Recognition of ☐☐LFA-1-derived Peptides by ICAM-1 Cell Receptors: Inhibitors of T-cell Adhesion, Chem Biol Drug Des 2007; 70, pp. 237-246.

\* cited by examiner

```
                        SEQUENCE LISTING

<160> NUMBER OF SEQ ID NOS: 114

<210> SEQ ID NO 1
    <211> LENGTH: 7
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 1

Ile Glu Leu Leu Gln Ala Arg
    1               5

<210> SEQ ID NO 2
    <211> LENGTH: 10
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 2

Ile Glu Leu Leu Gln Ala Arg Gly Ser Cys
    1               5                   10

<210> SEQ ID NO 3
    <211> LENGTH: 7
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 3

Ile Asp Leu Met Gln Ala Arg
    1               5

<210> SEQ ID NO 4
    <211> LENGTH: 10
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 4

Ile Asp Leu Met Gln Ala Arg Gly Ser Cys
    1               5                   10

<210> SEQ ID NO 5
    <211> LENGTH: 12
    <212> TYPE: PRT
    <213> ORGANISM: Artificial Sequence
    <220> FEATURE:
    <223> OTHER INFORMATION: Description of Artificial Sequence: Synthetic
          peptide
```

```
<400> SEQUENCE: 5

Gln Ile Thr Trp Ala Gln Leu Trp Asn Met Met Lys
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ile Thr Trp Ala Gln Leu Trp Asn Met Met Lys Gly Ser Cys
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Ala Phe Lys Ile Leu Val Val Ile Thr Phe Gly Glu Lys
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Ala Phe Lys Ile Leu Val Val Ile Thr Phe Gly Glu Lys Gly Ser
1               5                   10                  15

Cys

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Thr Asp Gly Glu Ala
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Thr Asp Gly Glu Ala Gly Ser Cys
1               5

<210> SEQ ID NO 11
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Gly Glu Ala Thr Asp
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Gly Glu Ala Thr Asp Gly Ser Cys
1               5

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Arg Arg Ala Ser Leu Gly Asp Gly Asp Ile Thr Trp Asp Gln Leu
1               5                   10                  15

Trp Asp Leu Met Lys
            20

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Ile Thr Trp Asp Gln Leu Trp Asn Val Met Asn
1               5                   10

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Gly Asn Ser Asn Ile Thr Trp Asp Gln Leu Trp Ser Ile Met Asn
1               5                   10                  15

Arg Gln Thr Thr
            20

<210> SEQ ID NO 16
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 16

Trp Thr Asp Thr His Ile Thr Trp Asp Gln Leu Trp His Phe Met Asn
1               5                   10                  15

Met Gly Glu Gln
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Pro Trp Asp Gln Ile Thr Trp Asp Gln Leu Trp Ile Ile Met Asn
1               5                   10                  15

Asn Gly Asp Gly
            20

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His Ile Thr Trp Asp Gln Leu Trp Leu Met Met Ser
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Leu Thr Trp Glu Gly Leu Trp Ile Leu Met Thr
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Gly Val Trp Gly Gly Leu Trp Ser Met Thr Trp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 21

Asp Tyr Ser Trp His Asp Leu Trp Phe Met Met Ser
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Lys Glu Asp Trp Leu Ala Leu Trp Arg Ile Met Ser Val Pro Asp
1               5                   10                  15

Glu Asn

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Asn Met Ser Trp Leu Glu Leu Trp Glu His Met Lys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Glu Gln Gln Trp Arg Asn Leu Trp Lys Met Met Ser
1               5                   10

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Gln Val Thr Trp Asn Asp Leu Trp Ser Val Met Asn Pro Glu Val
1               5                   10                  15

Val Asn

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ser Leu Ser Trp Leu Gln Leu Trp Asp Trp Met Lys
1               5                   10
```

```
<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Ile Thr Trp Asp Gln Leu Trp Asp Leu Met Lys
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Ile Thr Trp Asp Glu Leu Trp Lys Ile Met Asn
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Tyr Thr Trp Phe Glu Leu Trp Asp Met Met Gln
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Met Thr His Asp Leu Trp Leu Thr Leu Met Ser
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Ile Thr Trp Asp Gln Leu Trp Glu Val Met Asn
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 32

His Val Ser Trp Glu Gln Leu Trp Asp Ile Met Asn
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

His Ile Thr Trp Asp Gln Leu Trp Arg Ile Met Thr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Ile Ser Trp Asp Asp Leu Trp Ile Met Met Asn
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ile Thr Trp Asp Gln Leu Trp Asp Leu Met Tyr
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Glu Trp Thr Trp Asp Gln Leu Trp His Val Met Asn Pro Ala Glu
1               5                   10                  15

Ser Gln

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

His Arg Ala Glu Trp Leu Ala Leu Trp Glu Gln Met Ser Pro
1               5                   10

```
<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Lys Glu Asp Trp Leu Ala Leu Trp Arg Ile Met Ser Val
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Arg Lys Gln Trp Ile Glu Leu Trp Asn Ile Met Ser
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Trp Lys Leu Asp Thr Leu Asp Met Ile Trp Gln Asp
1               5                   10

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

His Ile Thr Trp Asp Gln Leu Trp Asn Val Met Leu Arg Arg Ala Ala
1               5                   10                  15

Ser Leu Gly

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Trp Cys Glu Tyr Leu Gly Gly Tyr Leu Arg Tyr Cys Ala
1               5                   10

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 43

Phe Glu Gly Phe Ser Phe Leu Ala Phe Glu Asp Phe Val Ser Ser Ile
1               5                   10                  15

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asn Asn Gln Lys Ile Val Asn Leu Lys Glu Lys Val Ala Gln Leu Glu
1               5                   10                  15

Ala

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asn Asn Gln Lys Ile Val Asn Ile Lys Glu Lys Val Ala Gln Ile Glu
1               5                   10                  15

Ala

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asn Asn Gln Lys Leu Val Asn Ile Lys Glu Lys Val Ala Gln Ile Glu
1               5                   10                  15

Ala

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Tyr Pro Ala Ser Tyr Gln Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48
```

Tyr Gln Ala Thr Pro Leu Pro
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Ser Leu Leu Ser Ala Ala
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Phe Ser Pro His Ser Arg Thr
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Pro Phe Leu Pro Thr Ala
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Cys Lys Leu Cys Ala Gln
1               5

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggtcggggtg agtttcgtgg tagggataat tctgtttggg tggtt            45

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Glu Trp Cys Glu Tyr Leu Gly Gly Tyr Leu Arg Cys Tyr Ala
1               5                   10

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Arg Gly Glu Phe Arg Gly Arg Asp Asn Ser Val Ser Val Val
1               5                   10                  15

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Thr Ser Val Ser Pro Ser Lys Val Ile
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Pro Ser Lys Val Ile Leu Pro Arg Gly Gly
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Pro Arg Gly Gly Ser Val Leu Val Thr Gly
1               5                   10

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Thr Ser Val Ser Pro Ser Lys Val Ile Leu Pro Arg Gly Gly Ser
1               5                   10                  15

Val Leu Val Thr Gly
            20

-continued

```
<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Tyr Arg Leu Ala Ile Arg Leu Asn Glu Arg
1               5                   10

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Tyr Arg Leu Ala Ile Arg Leu Asn Glu Arg Arg Glu Asn Leu Arg Ile
1               5                   10                  15

Ala Leu Arg Tyr
            20

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Glu Asn Leu Arg Ile Ala Leu Arg Tyr
1               5                   10

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Arg Ala Asn Ala Ala Leu Lys Ala Gly Glu Leu Tyr Lys Ser Ile
1               5                   10                  15

Leu Tyr

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Glu Leu Tyr Lys Ser Ile Leu Tyr
1               5

<210> SEQ ID NO 65
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Arg Ala Asn Ala Ala Leu Lys Ala Gly Glu Leu Tyr Lys Cys Ile
1               5                   10                  15

Leu Tyr

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Glu Leu Tyr Lys Cys Ile Leu Tyr
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Leu Asp Gly Asn Glu Ile Lys Arg
1               5

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala His Glu Glu Ile Ser Thr Thr Asn Glu Gly Val Met
1               5                   10

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asn Gly Val Phe Lys Tyr Arg Pro Arg Tyr Phe Leu Tyr Lys His Ala
1               5                   10                  15

Tyr Phe Tyr Pro Pro Leu Lys Arg Phe Pro Val Gln
            20                  25

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 70

Cys Gln Asp Ser Glu Thr Arg Thr Phe Tyr
1               5                   10

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Lys Lys Thr Leu Arg Thr
1               5

<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Leu Arg Ser Lys Ser Lys Lys Phe Arg Arg Pro Asp Ile Gln Tyr
1               5                   10                  15

Pro Asp Ala Thr Asp Glu Asp Ile Thr Ser His Met
            20                  25

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Gln Asn Pro Val Gln Pro
1               5

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Tyr Ile Arg Ile Ala Asp Thr Asn Ile Thr
1               5                   10

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys Glu Leu Asn Leu Val Tyr Thr
1               5

```
<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Ser Ile Thr Thr Ile Asp Val Pro Trp Asn Val
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Trp Arg Glu Pro Ser Phe Cys Ala Leu Ser
1               5                   10

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (16)..(16)
<223> OTHER INFORMATION: Bip

<400> SEQUENCE: 78

Ala Trp His Cys Thr Thr Lys Phe Pro His His Tyr Cys Leu Tyr Xaa
1               5                   10                  15

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (17)..(17)
<223> OTHER INFORMATION: Bip

<400> SEQUENCE: 79

Ala His Lys Cys Pro Trp His Leu Tyr Thr Thr His Tyr Cys Phe Thr
1               5                   10                  15

Xaa

<210> SEQ ID NO 80
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 80

Ala His Lys Cys Pro Trp His Leu Tyr Thr His Tyr Cys Phe Thr
1               5                   10                  15

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-hydroxyproline

<400> SEQUENCE: 81

Gly Arg Xaa Gly Glu Arg
1               5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-hydroxyproline

<400> SEQUENCE: 82

Gly Met Xaa Gly Glu Arg
1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-hydroxyproline

<400> SEQUENCE: 83

Gly Leu Xaa Gly Glu Asn
1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
```

```
<223> OTHER INFORMATION: 4-hydroxyproline

<400> SEQUENCE: 84

Gly Leu Xaa Gly Glu Arg
1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Leu Lys Gly Glu Asn
1               5

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-hydroxyproline
<220> FEATURE:
<221> NAME/KEY: MOD_RES
<222> LOCATION: (12)..(12)
<223> OTHER INFORMATION: 4-hydroxyproline

<400> SEQUENCE: 86

Gly Phe Xaa Gly Glu Arg Gly Val Glu Gly Pro Xaa Gly Pro Ala
1               5                   10                  15

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

His Val Trp Met Gln Ala Pro Gly Gly Gly Lys
1               5                   10

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Trp Tyr Arg Gly Arg Leu
1               5

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 89

Trp Thr Cys Ser Gly Asp Glu Tyr Thr Trp His Cys
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Trp Thr Cys Val Gly Asp His Lys Thr Trp Lys Cys
1               5                   10

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Trp His Cys Thr Thr Arg Phe Pro His His Tyr Cys Leu Tyr Gly
1               5                   10                  15

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Thr Trp Thr Trp Asn Gly Ser Ala Trp Thr Trp Asn Glu Gly Gly
1               5                   10                  15

Lys

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Thr Trp Thr Trp Asn Gly Thr Asn Trp Thr Arg Asn Asp Gly Gly
1               5                   10                  15

Lys

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Cys Val Trp Leu Trp Glu Gln Cys
1               5
```

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Cys Met Thr Ser Pro Trp Arg Cys
1               5

<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Cys Pro Gly Arg Val Met His Gly Leu His Leu Gly Asp Asp Glu Gly
1               5                   10                  15

Pro Cys

<210> SEQ ID NO 97
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Gly Gly
1

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Gly Gly Gly Gly
1               5

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Ser Gly Cys
1

<210> SEQ ID NO 100
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 100

Gly Ser Gly Ser Gly
1               5

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Lys Lys Gly Ser Gly
1               5

<210> SEQ ID NO 102
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Lys Lys Gly Cys
1

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Lys Lys Lys Gly Ser Gly
1               5

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Lys Lys Lys Gly Cys
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ile Glu Leu Leu Gln Ala Arg Gly Cys
1               5
```

```
<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ile Glu Leu Leu Gln Ala Arg
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ile Asp Leu Met Gln Ala Arg Gly Cys
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ile Glu Leu Leu Gln Ala Arg Gly Cys
1               5

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Ile Thr Trp Ala Gln Leu Trp Met Met Lys Gly Cys
1               5                   10

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asp Gly Glu Ala Thr Asp Gly Cys
1               5

<210> SEQ ID NO 111
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111
```

```
Lys Gly Ser Gly
1

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Lys Leu Trp Leu Leu Pro Lys
1               5

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Gln Asp Ser Glu Thr Arg Thr Phe Tyr
1               5                   10

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ile Thr Asp Gly Glu Ala Gly Cys
1               5
```

SELECTIN AND ICAM/VCAM PEPTIDE LIGAND CONJUGATES

CROSS REFERENCE TO RELATED APPLICATIONS

This application is a U.S. national stage of Application No. PCT/US2015/030424 filed May 12, 2015, which application claims the benefit of U.S. Application No. 61/992,056, filed May 12, 2014, the contents of which are incorporated herein by reference in their entirety.

STATEMENT AS TO FEDERALLY SPONSORED RESEARCH OR DEVELOPMENT

This invention was made with government support under T32DK101001 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Jun. 19, 2018, is named 4JR-209735-US_SL.txt and is 29,452 bytes in size.

BACKGROUND

This section introduces aspects that may help facilitate a better understanding of the disclosure. Accordingly, these statements are to be read in this light and are not to be understood as admissions about what is or is not prior art.

Intimal hyperplasia forms as a result of blood vessel damage and disease. In damaged vessels, platelets bind to and become activated on exposed collagen within the blood vessel. The activated platelets support thrombus formation, release inflammatory cytokines and recruit monocytes from the blood into the vessel tissue. The monocytes then secrete factors including cytokines that stimulate smooth muscle cell (SMC) migration into the intimal layer, and extracellular matrix (ECM) secretion, which results in intimal hyperplasia. Dysfunctional endothelium, which is present in all diabetic patients due to due to uremia and other metabolic disorders, supports platelet binding and activation similar to exposed collagen. In addition, dysfunctional and damaged endothelium supports leukocyte migration from blood into the blood vessel wall. Dysfunctional endothelium also loses cell-cell junctions, becomes leaky due to gaps between the cells, and potentially exposes underlying collagen in these gaps that is then accessible to platelet binding. Thus, exposed collagen present due to loss of endothelial cells (ECs), as a result of mechanical vessel damage during handling, and dysfunctional and damaged ECs support intimal hyperplasia.

Loss of glycocalyx, the anionic glycosaminoglycan layer covering the endothelium is a hallmark of dysfunctional endothelium and inflammation. Loss of the glycocalyx unmasks cell surface receptors including ICAM and VCAM, which are expressed in chronic inflammation and EC dysfunction. Glycocalyx loss also exposes receptors P-selectin and E-selectin, which are transiently expressed on the cell surface due to damage and inflammation, and chronically expressed in dysfunctional endothelium as is the case in diabetic patients. The selectins facilitate leukocyte rolling on the ECs, which is the first step to monocyte and neutrophil migration into the vessel wall. Following rolling, the leukocytes bind more firmly to ICAM and VCAM. They then migrate into the tissue where they release cytokines, and stimulate SMC migration to the intima and ECM synthesis. The end result is intimal hyperplasia, which prevents outward remodeling and can promote long-term thrombosis.

Leukocyte migration through the endothelium can also lead to tissue and organ infiltration, as in the case of sepsis. This large infiltration can lead to organ failure, and on a broad scale, multiple system organ failure.

SUMMARY

This disclosure addresses the issue of damaged/dysfunctional endothelium, by targeting the endothelial selectin and/or ICAM/VCAM receptors that are exposed to blood flow with peptide ligands that are conjugated to glycosaminoglycans (GAGs) such as dermatan sulfate. Accordingly, in one embodiment, provided herein is a peptide conjugate comprising a glycosaminoglycan and from about 1 to about 50 peptide ligands, wherein the peptide ligands bind to a selectin, an ICAM and/or a VCAM receptor. The peptide conjugate may also by referred to herein as an EC-SEAL conjugate. In certain embodiments, the EC-SEAL conjugate further comprises an alkyl tail bound to the glycosaminoglycan.

In some aspects, the glycosaminoglycan is dextran, chondroitin, chondroitin sulfate, dermatan, dermatan sulfate, heparan sulfate, heparin, keratin, keratan sulfate, or hyaluronic acid. In some aspects, the peptide(s) are covalently bonded to the glycosaminoglycan via a linker. In some aspects, the linker is N-[β-maleimidopropionic acid]hydrazide (BMPH), 3-(2-pyridyldithio)propionyl hydrazide (PDPH) or the peptide GSG. In some aspects, the EC-SEAL conjugate comprises from about 3 to about 50, or from 5 to about 40, peptide ligands. In some aspects, the peptide ligand comprises an amino acid sequence selected from: i) IELLQAR (SEQ ID NO: 1); IELLQARGSC (SEQ ID NO: 2); IDLMQAR (SEQ ID NO: 3); IDLMQARGSC (SEQ ID NO: 4); QITWAQLWNMMK (SEQ ID NO: 5); QITWAQLWNMMKGSC (SEQ ID NO: 6), NAFKILVVITFGEK (SEQ ID NO: 7); NAFKILVVITFGEKGSC (SEQ ID NO: 8); ITDGEA (SEQ ID NO: 9); ITDGEAGSC (SEQ ID NO: 10); DGEATD (SEQ ID NO: 11); or DGEATDGSC (SEQ ID NO: 12); or ii) a peptide comprising a sequence with at least about 80% sequence identity to the amino acid sequence of i) and capable of binding to selectin, ICAM and/or VCAM.

In some aspects, the EC-SEAL conjugate is administered to achieve a plasma concentration of peptide ligand from 20 µM to 1000 µM proximate the dysfunctional endothelium. In some aspects, the EC-SEAL conjugate is administered to achieve a plasma concentration of peptide ligand from 100 µM to 400 µM proximate the dysfunctional endothelium.

In some aspects, the EC-SEAL conjugate comprises from about 5 to about 40 peptide ligands that are capable of binding to selectin. In some aspects, the EC-SEAL conjugate comprises from about 5 to about 40 peptide ligands that are capable of binding to ICAM and/or VCAM. In some aspects, the EC-SEAL conjugate comprises from about 5 to about 20 peptide ligands capable of binding to selectin and from about 5 to about 20 peptide ligands capable of binding to ICAM and/or VCAM. In some aspects, the EC-SEAL conjugate comprises dermatan sulfate or chondroitin sulfate and from about 3 to about 25 peptide ligands, wherein the peptide ligands bind to selectin, ICAM and/or VCAM. In some aspects, the EC-SEAL conjugate comprises dermatan sulfate and about 10, 15, 20 or 30 peptide ligands, wherein the peptide ligands bind to selectin, ICAM and/or VCAM. In some aspects, the EC-SEAL conjugate comprises dermatan sulfate and about 10 peptide ligands capable of binding to a selectin and about 10 peptide ligands capable of binding to ICAM and/or VCAM.

One aspect of the disclosure is an EC-SEAL conjugate that includes a peptide ligand, a glycosaminoglycan, and an optional alkyl tail. Accordingly, the structure of such an EC-SEAL conjugate can be of the following formula:

$$(R)_m\text{-GAG-}(P)_n$$

wherein:

R is a linear or branched $C_{2-25}$ alkyl chain;

GAG is a glycosaminoglycan;

each P is independently a peptide of 3 to about 50 amino acids that comprises one or more selectin-binding unit, ICAM-binding unit and/or VCAM-binding unit;

n is an integer of from 1-50; and m is 0, 1, 2, or 3.

The GAG can be any glycosaminoglycan, such as such as alginate, agarose, dextran, chondroitin, dermatan, dermatan sulfate, heparin, heparan sulfate, keratin, hyaluronan, or a combination thereof.

Such an EC-SEAL conjugate can inhibit platelet activation, inhibit platelet binding to a mammalian blood vessel, inhibit intimal hyperplasia, inhibit inflammation in a mammalian blood vessel, inhibit thrombosis, inhibit vasospasm, stimulate endothelial cell proliferation, bind to exposed selectin, ICAM, VCAM, or combinations thereof in a mammalian blood vessel. For example, such EC-SEAL can inhibit or reduce the incidence of multiple organ failure in a hemolysis patient.

Accordingly, in one embodiment, the present disclosure provides methods for treating a patient suffering from a disease associated with endothelial dysfunction. Also provided, in one embodiment, is a method for treating or inhibiting endothelial dysfunction in a patient in need thereof. Another aspect of the disclosure is a method that involves contacting one or more endothelial cells with any of the EC-SEAL conjugates described herein.

Non-limiting examples of diseases associated with endothelial dysfunction include atherosclerosis, coronary artery disease, diabetes mellitus, hypertension, hypercholesterolemia, rheumatoid arthritis, systemic lupus erythematosus, glaucoma, uremia, sepsis, and organ failure. In some aspects, the administration is intravenous, intraperitoneal, topical or through an implanted device.

In some aspects, the endothelial dysfunction is characterized by permeated endothelial lining or damaged endothelial cells. In some aspects, the endothelial dysfunction is characterized by loss of glycocalyx. In some aspects, the endothelial dysfunction is characterized by a selectin protein expressed on the surface of endothelial cells and exposed to circulation. In some aspects, the site suffers from inflammation.

In one embodiment, the disclosure provides a method of inhibiting endothelial cell dysfunction comprising providing a EC-SEAL conjugate as provided herein; and administering the EC-SEAL to at least one dysfunctional endothelial cell, wherein the EC-SEAL is administered to inhibit production of selectin molecules on the dysfunctional endothelial cell.

In some aspects, the EC-SEAL conjugate as provided herein inhibits inflammatory responses in the cell. In some aspects, the EC-SEAL conjugate inhibits platelet binding. In some aspects, the EC-SEAL conjugate inhibits intimal hyperplasia. In some aspects, the EC-SEAL conjugate inhibits chronic inflammation. In some aspects, the EC-SEAL conjugate inhibits multiple system organ failure. In some aspects, the EC-SEAL conjugate treats glaucoma. In some aspects, the EC-SEAL conjugate stimulates endothelial cell proliferation.

Also provided, in one embodiment, is a method for preventing or reducing inflammation at a vascular site in a patient, wherein the site (a) comprises permeated endothelial lining or damaged endothelial cells, and (b) is not undergoing to recovering from a vascular intervention procedure, the method comprising administering to the patient a pharmaceutical composition comprising an effective amount of a EC-SEAL conjugate as provided herein.

In some aspects, the vascular intervention procedure comprises a percutaneous coronary intervention (PCI) procedure.

In some aspects, the patient is not undergoing or recovering from a vascular intervention procedure. In some aspects, the vascular intervention procedure comprises a percutaneous coronary intervention (PCI) procedure. In some aspects, the vascular intervention procedure comprises denuding a blood vessel.

In one embodiment, the present disclosure provides a compound for use in vascular intervention in a patient, said compound comprising a EC-SEAL conjugate wherein the EC-SEAL conjugate binds to a denuded vessel in the patient. In some aspects, the EC-SEAL conjugate inhibits platelet activation. In some aspects, the EC-SEAL conjugate inhibits platelet binding to the denuded vessel. In some aspects, the EC-SEAL conjugate inhibits intimal hyperplasia. In some aspects, the EC-SEAL conjugate inhibits inflammation resulting from denuding of the vessel.

In some aspects, the EC-SEAL conjugate inhibits thrombosis. In some aspects, the EC-SEAL conjugate inhibits vasospasm. In some aspects, the EC-SEAL conjugate stimulates endothelial cell proliferation. In some aspects, the EC-SEAL conjugate binds to exposed collagen on the denuded vessel.

DESCRIPTION OF THE FIGURES

FIG. 1A shows TNFα stimulated endothelial cells after such treatment (nuclei labeled with SYTOX-green) with the DS-QAR$_{20\text{-}biotin}$ bound (red), and yellow arrows to highlight cells with especially large coatings of DS-QAR$_{20\text{-}biotin}$ (red areas). FIG. 1B shows PBS stimulated endothelial cells treated with DS-QAR$_{20\text{-}biotin}$; showing that little binding of DS-QAR$_{20\text{-}biotin}$ occurs to cell that have not been stimulated with TNFα. Scale bars are 30 µm.

DETAILED DESCRIPTION

Figures 1A, 1B:
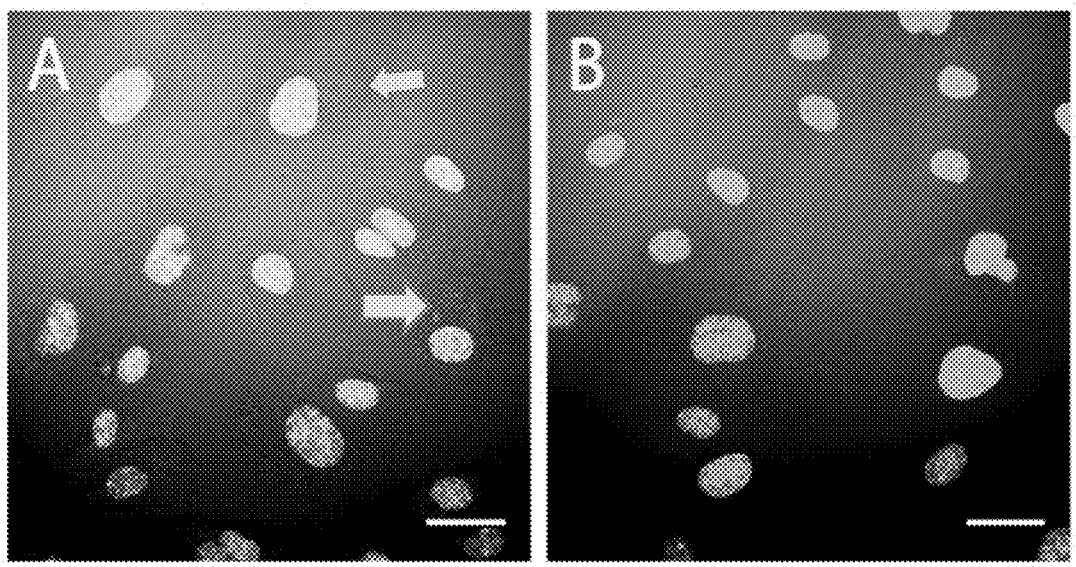
FIGS. 1A and 1B show images of human coronary endothelial cells (HAECs) that were stimulated with 5 ng/ml TNFα or an equivalent volume of PBS for 4 hours, then treated with 2 mg/ml biotin-EC-SEAL for 1 hour (see Example 2). The EC-SEAL molecule employed (DS-QAR$_{20\text{-}biotin}$) was a conjugate of a selectin ligand peptide (IELLQARGSC, SEQ ID NO:2), and oxidized dermatan sulfate. After such treatment, the cells were rinsed and fixed; then DS-QAR$_{20\text{-}biotin}$ binding to selectins on HAECs was probed with avidin-alexafluor.

Unless defined otherwise, all technical and scientific terms used herein have the same meaning as commonly understood by one of ordinary skill in the art to which this disclosure belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

As used herein, the term "composition" refers to a preparation suitable for administration to an intended patient for therapeutic purposes that contains at least one pharmaceutically active ingredient, including any solid form thereof. The composition may include at least one pharmaceutically acceptable component to provide an improved formulation of the compound, such as a suitable carrier.

Peptide Conjugates

The disclosure relates to peptide conjugates that protect the endothelial cell linings of blood vessels from injury, uremia, oxidative stress and inflammation. The peptide conjugates can form an S/E selectin-binding and ICAM-binding antineutrophil/monocyte luminal lining (EC-SEAL) that is especially useful for protection of endothelial cell linings of surgically affected vessels as well as catheterized vessels.

The EC-SEAL peptide conjugates include one or more peptide ligands that can bind to selectin, ICAM and/or VCAM. The peptide ligands are conjugated to a glycosaminoglycan (GAG) such as dermatan sulfate, and the conjugate can also include from one to about three hydrophobic tail(s) (e.g., an alkyl tail).

The EC-SEAL conjugates described herein can comprise one or more types of peptide ligands, such that the EC-SEAL conjugate is capable of binding to selectin, ICAM and/or VCAM. For example, included herein are EC-SEAL conjugates which comprise both selectin-binding peptides and ICAM-binding peptides. Also included are EC-SEAL conjugates which comprise both selectin-binding peptides and VCAM-binding peptides, or EC-SEAL conjugates which comprise both ICAM-binding peptides and VCAM-binding peptides. In addition, the peptide ligands may comprise one or more selectin, ICAM and/or VCAM-binding units (or sequences) within a single peptide. Accordingly, in one embodiment, disclosed herein is an EC-SEAL conjugate comprising peptides having both a selectin-binding unit (or sequence) and a ICAM-binding unit (or sequence). Also included are EC-SEAL conjugates which comprise both a selectin-binding unit (or sequence) and a VCAM-binding unit (or sequence). Also included are EC-SEAL conjugates which comprise both an ICAM-binding unit (or sequence) and a VCAM-binding unit (or sequence).

The peptide ligands are synthetic peptides that can have a variety of structures. As used herein, the term "peptide ligand" is intended to refer a chain of amino acids linked by peptide (or amide) bonds. In one embodiment, the peptide ligand comprises from about 3 to about 120 amino acids, or from about 3 to about 110 amino acids, or from about 3 to about 100 amino acids, or from about 3 to about 90 amino acids, or from about 3 to about 80 amino acids, or from about 3 to about 70 amino acids, or from about 3 to about 60 amino acids, or from about 3 to about 50 amino acids, or from about 3 to about 40 amino acids, or from about 5 to about 120 amino acids, or from about 5 to about 100 amino acids, or from about 5 to about 90 amino acids, or from about 5 to about 80 amino acids, or from about 5 to about 70 amino acids, or from about 5 to about 60 amino acids, or from about 5 to about 50 amino acids, or from about 5 to about 40 amino acids, or from about 5 to about 30 amino acids, or from about 5 to about 20 amino acids, or from about 5 to about 10 amino acids. Although the peptide ligands can be of varying lengths, typically, the peptide ligands have about 5 to about 40 amino acids. Examples of useful peptide ligands include the following peptide sequences (or units), which can bind to selectins: IELLQAR (SEQ ID NO:1); IELLQARGSC (SEQ ID NO:2); IDLMQAR (SEQ ID NO:3); IDLMQARGSC (SEQ ID NO:4); QITWAQLWNMMK (SEQ ID NO:5); QITWAQLWNMMKGSC (SEQ ID NO:6), and combinations thereof. The selectin can be a S-, P- or E-selectin. Various methods for screening peptide sequences for E-selectin-binding affinity (or a E-selectin-binding unit) are routine in the art (see, e.g., Martens, C. L. et al. J. Biol. Chem. 1995, 270(36), 21129-21136; and Koivunen, E. et al. J. Nucl. Med. 1999, 40, 883-888).

Other peptide sequences shown to have E-selectin-binding affinity (or an E-selectin-binding unit) which can be used in the EC-SEAL conjugates and methods disclosed herein include but are not limited to, LRRASLGDGDITWDQLWDLMK (SEQ ID NO: 13), HITWDQLWNVMN (SEQ ID NO: 14), QITWAQLWNMMK (SEQ ID NO: 5), YGNSNITWDQLWSIMNRQTT (SEQ ID NO: 15), WTDTHITWDQLWHFMNMGEQ (SEQ ID NO: 16), EPWDQITWDQLWIIMNNGDG (SEQ ID NO: 17), HITWDQLWLMMS (SEQ ID NO: 18), DLTWEGLWILMT (SEQ ID NO: 19), RGVWGGLWSMTW (SEQ ID NO: 20), DYSWHDLWFMMS (SEQ ID NO: 21), KKEDWLALWRIMSVPDEN (SEQ ID NO: 22), RNMSWLELWEHMK (SEQ ID NO: 23), KEQQWRNLWKMMS (SEQ ID NO: 24), SQVTWNDLWSVMNPEVVN (SEQ ID NO: 25) and RSLSWLQLWDWMK (SEQ ID NO: 26), (see, e.g., Martens, C. L. et al. J. Biol. Chem. 1995, 270(36), 21129-21136), DITWDQLWDLMK (SEQ ID NO: 27) (see, e.g., Koivunen, E. et al. J. Nucl. Med. 1999, 40, 883-888), DITWDELWKIMN (SEQ ID NO: 28), DYTWFELWDMMQ (SEQ ID NO: 29), DMTHDLWLTLMS (SEQ ID NO: 30), EITWDQLWEVMN (SEQ ID NO: 31), HVSWEQLWDIMN (SEQ ID NO: 32), HITWDQLWRIMT (SEQ ID NO: 33), DISWDDLWIMIVIN (SEQ ID NO: 34), QITWDQLWDLMY (SEQ ID NO: 35), RNMSWLELWEHMK (SEQ ID NO:), AEWTWDQLWHVMNPAESQ (SEQ ID NO: 36), HRAEWLALWEQMSP (SEQ ID NO: 37), KKEDWLALWRIMSV (SEQ ID NO: 38), KRKQWIELWNIMS (SEQ ID NO: 39), WKLDTLDMIWQD (SEQ ID NO: 40) and HITWDQLWNVMLRRAASLG (SEQ ID NO: 41) (see, e.g., Simanek, E. E. Chem. Rev. 1998, 98, 833-862), or combinations thereof, wherein each is hereby incorporated by reference in its entirety.

Various methods for screening peptide sequences for ICAM-binding affinity (or a ICAM-binding unit) are routine in the art (see, e.g., Martens, C. L. et al. J. Biol. Chem. 1995, 270(36), 21129-21136; and Koivunen, E. et al. J. Nucl. Med. 1999, 40, 883-888). Examples of useful peptide ligands that can bind ICAM include the following: NAFKILVVITFGEK (SEQ ID NO:7); NAFKILVVITFGEKGSC (SEQ ID NO:8); ITDGEA (SEQ ID NO:9); ITDGEAGSC (SEQ ID NO:10); DGEATD (SEQ ID NO:11); DGEATDGSC (SEQ ID NO:12), and combinations thereof.

Other peptide sequences shown to have ICAM-binding affinity (or a ICAM-binding unit) which can be used in the EC-SEAL conjugates and methods disclosed herein include but are not limited to, EWCEYLGGYLRYCA (SEQ ID NO: 42) (see, e.g., Welply, J. K. et al. Proteins: Structure, Function, and Bioinformatics 1996, 26(3): 262-270), FEGFSFLAFEDFVSSI (SEQ ID NO: 43) (see, e.g., US Publication No. WO2014059384), NNQKIVNLKEK-VAQLEA (SEQ ID NO: 44), NNQKIVNIKEKVAQIEA (SEQ ID NO: 45), NNQKLVNIKEKVAQIEA (SEQ ID NO: 46), YPASYQR (SEQ ID NO: 47), YQATPLP (SEQ ID NO: 48), GSLLSAA (SEQ ID NO: 49), FSPHSRT (SEQ ID NO: 50), YPFLPTA (SEQ ID NO: 51) and GCKLCAQ (SEQ ID NO: 52) (see, e.g., U.S. Pat. No. 8,926,946), GGTCGGGGTGAGTTTCGTGGTAGGGATAATTCT-GTTTGGGTGGTT (SEQ ID NO: 53), EWCEYLGGYLR-CYA (SEQ ID NO: 54) (see, e.g., Koivunen, E. et al. J. Nucl. Med. 1999, 40, 883-888), GRGEFRGRDNSVSVV (SEQ ID NO: 55) (see, e.g., CN Publication No. CN1392158), QTSVSPSKVI (SEQ ID NO. 56), PSKVILPRGG (SEQ ID NO. 57), LPRGGSVLVTG (SEQ ID NO. 58), and QTS-VSPSKVILPRGGSVLVTG (SEQ ID NO. 59) (see, e.g., Tibbetts, S. A. et al. Peptides 21 (2000) 1161-1167), and combinations thereof, wherein each is hereby incorporated by reference in its entirety.

Various methods for screening peptide sequences for VCAM-binding affinity (or a VCAM-binding unit) are routine in the art (see, e.g., Martens, C. L. et al. J. Biol. Chem. 1995, 270(36), 21129-21136; and Koivunen, E. et al. J. Nucl. Med. 1999, 40, 883-888). Other peptide sequences shown to have VCAM-binding affinity (or a VCAM-binding domain) which can be used in the EC-SEAL conjugates and methods disclosed herein include but are not limited to, YRLAIRLNER (SEQ ID NO: 60), YRLAIRLNERRENL-RIALRY (SEQ ID NO: 61) and RENLRIALRY (SEQ ID NO: 62) (see, e.g., EP Publication No. EP1802352), and combinations thereof, which is hereby incorporated by reference in its entirety.

Variability can be present in the peptide ligand sequence. For example, the synthetic peptide ligands described herein can be modified by the inclusion of one or more conservative amino acid substitutions. As is well known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced. Accordingly, any peptide sequence described herein can be modified such that a sequence having at least about 80% sequence identity, or at least about 83% sequence identity, or at least about 85% sequence identity, or at least about 90% sequence identity, or at least about 95% sequence identity, or at least about 98% sequence identity thereto is incorporated in the EC-SEAL conjugate, provided the sequence is capable of binding to selectin, ICAM and/or VCAM. Accordingly, in certain embodiments, the peptide ligands can have, for example, amino acid sequences with 80%, 85%, 90%, 95%, or 98% homology with to any of the amino acid sequences.

In one embodiment, the peptide ligand, or the binding unit of the peptide, binds to selectin, ICAM and/or VCAM with a dissociation constant ($K_d$) of less than about 1 mM, or less than about 900 µM, or less than about 800 µM, or less than about 700 µM, or less than about 600 µM, or less than about 500 µM, or less than about 400 µM, or less than about 300 µM, or less than about 200 µM, or less than about 100 µM.

In some embodiments, the EC-SEAL conjugate further comprises one or more peptide ligand(s) having a collagen-binding unit. The collagen-binding unit can be located within the same or different peptide as the selectin, ICAM and/or VCAM binding unit. Accordingly, in some embodiments, the peptide ligand comprises one or more selectin, ICAM and/or VCAM-binding units and a collagen-binding unit. The collagen-binding unit can have amino acid homology with a portion of a protein normally or not normally involved in collagen fibrillogenesis. In some embodiments, these units have homology or sequence identity to the amino acid sequence of a small leucine-rich proteoglycan, a platelet receptor sequence, or a protein that regulates collagen fibrillogenesis. In various embodiments, the collagen-binding unit comprises an amino acid sequence selected from RRA-NAALKAGELYKSILY (SEQ ID NO: 63), GELYKSILY (SEQ ID NO: 64), RRANAALKAGELYKCILY (SEQ ID NO: 65), GELYKCILY (SEQ ID NO: 66), RLDGNEIKR (SEQ ID NO: 67), AHEEISTTNEGVM (SEQ ID NO: 68), NGVFKYRPRYFLYKHAYFYPPLKRFPVQ (SEQ ID NO: 69), CQDSETRTFY (SEQ ID NO: 70), TKKTLRT (SEQ ID NO: 71), GLRSKSKKFRRPDIQYPDATDEDITSHM (SEQ ID NO: 72), SQNPVQP (SEQ ID NO: 73), SYIR-IADTNIT (SEQ ID NO: 74), KELNLVYT (SEQ ID NO: 75), or GSITTIDVPWNV (SEQ ID NO: 76); or a sequence having at least about 80% sequence identity, or at least about 83% sequence identity, or at least about 85% sequence identity, or at least about 90% sequence identity, or at least about 95% sequence identity, or at least about 98% sequence identity thereto, provided the sequence is capable of binding to collagen.

In certain embodiments, the collagen-binding unit comprises an amino acid sequence that has at least about 80%, or at least about 83%, or at least about 85%, or at least about 90%, or at least about 95%, or at least about 98%, or at least about 100% sequence identity with the collagen-binding domain(s) of the von Willebrand factor (vWF) or a platelet collagen receptor as described in Chiang, T. M., et al. J. Biol. Chem., 2002, 277: 34896-34901, Huizinga, E. G. et al., Structure, 1997, 5: 1147-1156, Romijn, R. A., et al., J. Biol. Chem., 2003, 278: 15035-15039, and Chiang, et al., Cardio. & Haemato. Disorders-Drug Targets, 2007, 7: 71-75, each incorporated herein by reference. A non-limiting example is WREPSFCALS (SEQ ID NO: 77), derived from vWF.

Various methods for screening amino acid sequences for collagen-binding affinity (or a collagen-binding domain) are routine in the art. Other amino acid sequences shown to have collagen-binding affinity which can be used in the peptidoglycans and methods disclosed herein include but are not limited to, βAWHCTTKFPHHYCLYBip (SEQ ID NO: 78), βAHKCPWHLYTTHYCFTBip (SEQ ID NO: 79), βAHKCPWHLYTHYCFT (SEQ ID NO: 80), etc., where Bip is biphenylalanine and PA is beta-alanine (see, Abd-Elgaliel, W. R., et al., Biopolymers, 2013, 100(2), 167-173), GROGER (SEQ ID NO: 81), GMOGER (SEQ ID NO: 82), GLOGEN (SEQ ID NO: 83), GLOGER (SEQ ID NO: 84), GLKGEN (SEQ ID NO: 85), GFOGERGVEGPOGPA (SEQ ID NO: 86), etc., where 0 is 4-hydroxyproline (see, Raynal, N., et al., J. Biol. Chem., 2006, 281(7), 3821-3831), HVWMQAPGGGK (SEQ ID NO: 87) (see, Helms, B. A., et al., J. Am. Chem. Soc. 2009, 131, 11683-11685), WREPSFCALS (SEQ ID NO: 77) (see, Takagi, J., et al., Biochemistry, 1992, 31, 8530-8534), WYRGRL (SEQ ID NO: 88), etc. (see, Rothenfluh D. A., et al., Nat Mater. 2008, 7(3), 248-54), WTCSGDEYTWHC (SEQ ID NO: 89), WTCVGDHKTWKC (SEQ ID NO: 90), QWHCTTRFPHHYCLYG (SEQ ID NO: 91), etc. (see, U.S. 2007/0293656), STWTWNGSAWTWNEGGK (SEQ ID NO: 92), STWTWNGTNWTRNDGGK (SEQ ID NO: 93), etc. (see, WO/2014/059530), CVWLWEQC (SEQ ID NO: 94) (see, Depraetere H., et al., Blood. 1998, 92, 4207-4211; and Duncan R., Nat Rev Drug Discov, 2003, 2(5), 347-360), CMTSPWRC (SEQ ID NO: 95), etc. (see, Vanhoorelbeke, K., et al., J. Biol. Chem., 2003, 278, 37815-37821), CPGRVMHGLHLGDDEGPC (SEQ ID NO: 96) (see, Muzzard, J., et al., PLoS one. 4 (e 5585) I-10), KLWLLPK (SEQ ID NO: 112) (see, Chan, J. M., et al., Proc Natl Acad Sci U.S.A., 2010, 107, 2213-2218), and CQDSETRTFY (SEQ ID NO: 113), etc. (see, U.S. 2013/0243700), wherein each is hereby incorporated by reference in its entirety.

A "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of amino acid abbreviations and illustrative conservative amino acid substitutions are given in Table 1.

TABLE 1

| Full Name | Abbreviation (3 Letter) | Abbreviation (1 Letter) | Replace With |
|---|---|---|---|
| For Amino Acid | | | |
| Alanine | Ala | A | D-Ala, Gly, Aib, β-Ala, L-Cys, D-Cys |
| Arginine | Arg | R | D-Arg, Lys, D-Lys, Orn D-Orn |
| Asparagine | Asn | N | D-Asn, Asp, D-Asp, Glu, D-Glu Gln, D-Gln |
| Aspartic Acid | Asp | D | D-Asp, D-Asn, Asn, Glu, D-Glu, Gln, D-Gln |
| Cysteine | Cys | C | D-Cys, S-Me-Cys, Met, D-Met, Thr, D-Thr |
| Glutamine | Gln | Q | D-Gln, Asn, D-Asn, Glu, D-Glu, Asp, D-Asp |
| Glutamic Acid | Glu | E | D-Glu, D-Asp, Asp, Asn, D-Asn, Gln, D-Gln |
| Glycine | Gly | G | Ala, D-Ala, Pro, D-Pro, Aib, β-Ala |
| Histidine | His | H | |
| Isoleucine | Ile | I | D-Ile, Val, D-Val, Leu, D-Leu, Met, D-Met |
| Leucine | Leu | L | Val, D-Val, Met, D-Met, D-Ile, D-Leu, Ile |
| Lysine | Lys | K | D-Lys, Arg, D-Arg, Orn, D-Orn |
| Methionine | Met | M | D-Met, S-Me-Cys, Ile, D-Ile, Leu, D-Leu, Val, D-Val |
| Phenylalanine | Phe | F | D-Phe, Tyr, D-Tyr, His, D-His, Trp, D-Trp |
| Proline | Pro | P | D-Pro |
| Serine | Ser | S | D-Ser, Thr, D-Thr, allo-Thr, L-Cys, D-Cys |
| Threonine | Thr | T | D-Thr, Ser, D-Ser, allo-Thr, Met, D-Met, Val, D-Val |
| Tryptophan | Trp | W | |
| Tyrosine | Tyr | Y | D-Tyr, Phe, D-Phe, His, D-His, Trp, D-Trp |
| Valine | Val | V | D-Val, Leu, D-Leu, Ile, D-Ile, Met, D-Met |

Non-conservative substitutions in the peptide ligands can also be present provided that these do not excessively affect the binding activity of the peptide and/or reduce its effectiveness in inhibiting any of the following: platelet activation, platelet binding to endothelium, thrombosis, inflammation resulting from denuding the endothelium, intimal hyperplasia, and/or vasospasm, or its effectiveness in stimulating endothelial cell proliferation or in binding to a denuded vessel.

The glycosaminoglycan (abbreviated GAG or glycan) attached to the synthetic peptide ligand(s) can be selected from the group consisting alginate, agarose, dextran, chondroitin, dermatan, dermatan sulfate, heparin, heparan sulfate, keratin, and hyaluronan. In one embodiment, the glycan is selected from the group consisting of dermatan sulfate, dextran, and heparin. In some embodiments the glycan is dermatan sulfate. Dermatan sulfate is a natural glycosaminoglycan found mostly in skin, but also in blood vessels, heart valves, tendons, lungs and intestinal mucosa. In addition to its role as a major constituent of the skin and other organs, dermatan sulfate is believed to play a part in repairing wounds, regulating the coagulation of blood, and responding to infections, though its role in these processes is not well understood.

The peptide ligand(s) can be directly linked to the glycosaminoglycan, or linked to the glycosaminoglycan via a linker. The linker may include one or more bivalent fragments selected independently in each instance from the group consisting of alkylene, heteroalkylene, cycloalkylene, cycloheteroalkylene, arylene, and heteroarylene each of which is optionally substituted. As used herein heteroalkylene represents a group resulting from the replacement of one or more carbon atoms in a linear or branched alkylene group with an atom independently selected in each instance from the group consisting of oxygen, nitrogen, phosphorus and sulfur.

Each glycosaminoglycan can have from about 1 to about 50, or from about 3 to about 50, peptide ligands linked thereto. In some embodiments, each glycosaminoglycan can be covalently bound to at least 3 peptide ligands, or at least 5 peptide ligands, or at least 8 peptide ligands, or at least 10 peptide ligands, or at least 15 peptide ligands, or at least 20 peptide ligands, or at least 25 peptide ligands. In some embodiments, each glycosaminoglycan can be covalently bound to about 5 to about 45 peptide ligands, or to about 7 to about 45 peptide ligands, or to about 8 to about 40 peptide ligands, or to about 10 to about 35 peptide ligands, or to about 10 to about 30 peptide ligands, or to about 15 to about 30 peptide ligands.

The EC-SEAL conjugates can also include from 1 to about 3 alkyl tails, which can be useful for regulating the hydrophobicity of the EC-SEAL conjugates. For example, nanoparticulate EC-SEAL conjugates can form micelles when alkyl tails are employed. EC-SEAL micelles form nanoparticles that slowly dissociate in vivo to deliver additional free EC-SEAL to vascular sites such as to the lumen of fistulae. As used herein, the term "alkyl tail" is intended to refer to a substantially hydrophobic alkyl chain. The alkyl chain typically comprises a saturated monovalent hydrocarbyl group having from 2 to about 25 carbon atoms, more particularly from 2 to about 18 carbon atoms. The alkyl chain can comprise linear, branched or cyclic groups, and can comprise sites of unsaturation and/or other optional functional groups, provided that the alkyl chain (or alkyl tail) is substantially hydrophobic. The alkyl tail employed is generally a two to eighteen carbon ($C_{2-18}$) alkyl chain. In some embodiments, the alkyl tail (i.e., alkyl chain) has 2-25 carbon atoms ($C_{2-25}$), or 3-25 carbon atoms ($C_{3-25}$), or 4-14 carbon atoms ($C_{4-14}$), or 5-12 carbon atoms ($C_{5-12}$). For example, alkyl chains such as isopropyl (C3), butyl (C4), hexyl (C6), octyl (C8), decyl (C10), or dodecyl (C12) can be employed. The alkyl chain (i.e., alkyl tail) can be linked to a functional group of the glycosaminoglycan. In some embodiments, it is convenient to employ an ether, ester, amide, amino, or acyl linkage between the alkyl tail and the glycosaminoglycan.

Thus, the EC-SEAL conjugates can have structures of the following formula:

$$(R)_m\text{-GAG-}(P)_n$$

wherein:

R is a linear or branched $C_{2-25}$ alkyl chain;

GAG is a glycosaminoglycan;

each P is independently a peptide of 3 to about 50 amino acids that comprises one or more selectin-binding unit, ICAM-binding unit and/or VCAM-binding unit;

n is an integer of from 1-50; and m is 0, 1, 2, or 3.

Methods of Preparation

The EC-SEAL conjugates can be made by available procedures, or any of the procedures described herein. For example, the synthetic peptide ligand(s) can be synthesized according to solid phase peptide synthesis protocols that are available to persons of skill in the art. In one embodiment a peptide precursor is synthesized on a solid support according to the well-known Fmoc protocol, cleaved from the support with trifluoroacetic acid and purified by chromatography according to methods available to persons skilled in the art.

The synthetic peptide ligand can also be synthesized utilizing the methods of biotechnology that are available to persons skilled in the art. In one embodiment a DNA sequence that encodes the amino acid sequence for the desired peptide ligand is ligated by recombinant DNA techniques known to persons skilled in the art into an expression cassette or expression vector (for example, a plasmid that incorporates an affinity tag for affinity purification of the peptide), a host cell is transfected or transformed with the expression cassette or the expression vector to permit recombinant expression of the peptide ligand, and the peptide is then isolated from the host organism or the growth medium according to methods known by persons skilled in the art (e.g., by affinity purification). Recombinant DNA technology methods are described in Sambrook et al., "Molecular Cloning: A Laboratory Manual," 3rd Edition, Cold Spring Harbor Laboratory Press, (2001), incorporated herein by reference, and are well-known to the skilled artisan.

A peptide (or a polypeptide or peptide region) has a certain percentage (for example, at least about 60%, or at least about 65%, or at least about 70%, or at least about 75%, or at least about 80%, or at least about 83%, or at least about 85%, or at least about 90%, or at least about 95%, or at least about 98% or at least about 99%) of "sequence identity" to another sequence means that, when aligned, that percentage of bases (or amino acids) are the same in comparing the two sequences. It is noted that, for any sequence ("reference sequence") disclosed in this application, sequences having at least about 60%, or at least about 65%, or at least about 70%, or at least about 75%, or at least about 80%, or at least about 83%, or at least about 85%, or at least about 90%, or at least about 95%, or at least about 98% or at least about 99% sequence identity to the reference sequence are also within the disclosure. Likewise, the present disclosure also includes sequences that have one, two, three, four, or five substitution, deletion or addition of amino acid residues or nucleotides as compared to the reference sequences.

The synthetic peptide ligand can be conjugated to a glycan by reacting a free amino group of the peptide with an aldehyde function of the glycan in the presence of a reducing agent, utilizing methods known to persons skilled in the art, to yield the peptide glycan conjugate. In one embodiment an aldehyde function of the glycan (e.g. polysaccharide or glycosaminoglycan) is formed by reacting the glycan with sodium metaperiodate according to methods known to persons skilled in the art.

Hydrophobication of the glycan can be achieved by conjugating a suitably functionalized glycan (e.g., a glycan containing an amine functional group) with a hydrophobic moiety (e.g., glycidyl ether conjugates of alkyl chains, such as isopropyl (C3), butyl (C4), hexyl (C6), octyl (C8), decyl (C10), or dodecyl (C12) glycidyl ether). Although alkyl chains are typically utilized for hydrophobication of the EC-SEAL conjugate, it is contemplated that other functional groups can also be incorporated (e.g., amino, thio, ether, etc.) in the alkyl tail.

The synthetic peptide ligand can be conjugated to a glycan by reacting an aldehyde function of the glycan with a crosslinker, e.g., 3-(2-pyridyldithio)propionyl hydrazide (PDPH), to form an intermediate glycan and further reacting the intermediate glycan with a peptide containing a free thiol group to yield the peptide glycan conjugate. In any of the various embodiments described herein, the sequence of the peptide may be modified to include a glycine-cysteine segment to provide an attachment point for a glycan or a glycan-linker conjugate. In any of the embodiments described herein, the crosslinker can be N-[β-Maleimidopropionic acid]hydrazide (BMPH).

Although specific embodiments have been described in the preceding paragraphs, the EC-SEAL conjugates described herein can be made by using any art-recognized method for conjugation of the peptide to the glycan (e.g., a polysaccharide or glycosaminoglycan). This can include covalent, ionic, or hydrogen bonding, either directly or indirectly via a linking group such as a divalent linker. The conjugate is typically formed by covalent bonding of the peptide to the glycan through the formation of amide, ester or imino bonds between acid, aldehyde, hydroxy, amino, or hydrazo groups on the respective components of the conjugate. All of these methods are known in the art or are further described in the Examples section of this disclosure or in Hermanson G. T., Bioconjugate Techniques, Academic Press, pp. 169-186 (1996), incorporated herein by reference. The linker typically comprises about 1 to about 30 carbon atoms, more typically about 2 to about 20 carbon atoms. Lower molecular weight linkers (i.e., those having an approximate molecular weight of about 20 to about 500) are typically employed.

In addition, structural modifications of the linker portion of the conjugates are contemplated herein. For example, amino acids may be included in the linker and a number of amino acid substitutions may be made to the linker portion of the conjugate, including but not limited to naturally occurring amino acids, as well as those available from conventional synthetic methods. In another aspect, beta, gamma, and longer chain amino acids may be used in place of one or more alpha amino acids. In another aspect, the linker may be shortened or lengthened, either by changing the number of amino acids included therein, or by including more or fewer beta, gamma, or longer chain amino acids. Similarly, the length and shape of other chemical fragments of the linkers described herein may be modified.

Accordingly, in any of the embodiments described herein, any one or more of the synthetic peptide ligand(s) may have a spacer sequence comprising from one to about five amino acids. It is contemplated that any amino acid, natural or unnatural, can be used in the spacer sequence, provided that the spacer sequence does not significantly interfere with the intended binding of the peptide. Exemplary spacers include, but are not limited to, short sequences comprising from one to five glycine units (e.g., G, GG, GGG, GGGG (SEQ ID NO: 97), or GGGGG (SEQ ID NO: 98)), optionally comprising cysteine (e.g., GC, GCG, GSGC (SEQ ID NO: 99), or GGC) and/or serine (e.g., GSG, or GSGSG (SEQ ID NO: 100)), or from one to five arginine units (e.g., R, RR, RRR, etc.). The spacer can also comprise non-amino acid moieties, such as polyethylene glycol (PEG), 6-aminohexanoic acid, or combinations thereof, with or without an amino acid spacer. The spacer can be attached to either the C-terminus or the N-terminus of the peptide to provide a point of attachment for a glycan or a glycan-linker conjugate.

In certain embodiments, the spacer comprises more than one binding site (may be linear or branched), thus creating a branched construct. The binding sites on the spacer can be the same or different, and can be any suitable binding site, such as an amine or carboxylic acid moiety, such that a desired peptide sequence can be bound thereto (e.g. via an amide bond). Thus in certain embodiments, the spacer contains one or more lysine, glutamic acid or aspartic acid residue. Such constructs can provide peptides having more than one selectin, ICAM and/or VCAM-binding unit of the formula $P_nL$, where P is a selectin, ICAM and/or VCAM-binding sequence, L is a spacer and n is an integer from 2 to about 10, or from 2 to 8, or from 2 to 6, or from 2 to 5, or from 2 to 4, or 2, or 3, or 4, or 5, or 6, or 7, or 8, or 9, or 10. For example, the spacer L can be an amino acid sequence such as KGSG (SEQ ID NO: 111), KGC, KKGSG (SEQ ID NO: 101), KKGC (SEQ ID NO: 102), KKKGSG (SEQ ID NO: 103), or KKKGC (SEQ ID NO: 104), etc., providing 2, 3, or 4 binding sites.

In EC-SEAL conjugates described herein, the peptide ligands can be bound to the glycan at any suitable point of attachment, such as for example, the C-terminus, the N-terminus or via a side chain on an amino acid. For example, a peptide may be bound to the glycan via a side chain of an amino acid of the peptide, such as the side of a glutamic acid or aspartic acid residue. In addition, the peptide ligands can be linear, branched or can contain one or more cyclic peptide sequences.

Methods of Using

The EC-SEAL conjugates can be used to inhibit platelet binding to endothelium, inhibit binding of other cells in blood to exposed epithelium, inhibit platelet activation, inhibit thrombosis, inhibit inflammation resulting from denuding the endothelium, inhibit intimal hyperplasia, and/or inhibit vasospasm. EC-SEAL conjugates described herein can also stimulate endothelial cell proliferation and can bind to the surface of blood vessels. In any of these embodiments, these aforementioned effects can occur during a vascular intervention procedure, such as a catheter-based procedure. In any of these embodiments, any of the above-described EC-SEAL conjugates can be used.

The present disclosure, in one embodiment, provides compositions and methods for treating a patient suffering from a disease associated with endothelial dysfunction. The present disclosure is also directed to inhibiting one or more of platelet binding to endothelium, platelet activation, thrombosis, inflammation resulting from denuding the endothelium, intimal hyperplasia, and/or vasospasm, or its effectiveness in stimulating endothelial cell proliferation or in binding to a denuded vessel, comprising administering an effective amount of a composition provided herein to a patient in need thereof. The compositions, in some embodiments, include an EC-SEAL conjugate of the present disclosure.

EC-SEAL conjugates as provided herein can reduce the inflammatory impact of endothelial dysfunction or injury, in both acute and chronic diseases. It is contemplated that such conjugates inhibit or reduce platelet binding to the dysfunctional endothelium and thus reduce platelet-mediated inflammation. Inflammation can be activated through platelet processes such as platelet-platelet binding, platelet-leukocyte binding, facilitation of leukocyte diapedesis, or simply release from platelets of local and regional cytokines.

Also provided, in some embodiments, is a method for preventing or reducing inflammation at a vascular site suffering from endothelial dysfunction. The method entails administering to the site a pharmaceutical composition that includes an EC-SEAL conjugate of the present disclosure.

As described herein, the EC-SEAL conjugates target the endothelial selectin and ICAM/VCAM receptors that are exposed to blood flow, where they can remain bound for a sufficient amount of time to prevent platelet binding to the denuded endothelium and, consequently, prevent platelet activation, thrombosis, inflammation resulting from denuding the endothelium, intimal hyperplasia, and vasospasm. Therefore, these EC-SEAL conjugates can inhibit inflammatory responses by inhibiting the production of selectins or ICAMs/VCAMs in dysfunctional endothelial cells.

The term "endothelial dysfunction" is also referred to as "endothelial cell (EC) dysfunction," "dysfunctional endothelium," or "dysfunctional endothelial cells." Endothelial dysfunction can be determined with unmasking or exposure of ICAM and VCAM receptors or selectin receptors on the cell surface of an endothelial cell. P-selectin and E-selectin are examples of selectin receptors exposed which are transiently expressed on the cell surface due to damage and inflammation, and chronically expressed in dysfunctional endothelium.

In some embodiments, endothelial dysfunction is characterized with permeated endothelial lining or damaged endothelial cells. In some embodiments, the endothelial dysfunction is characterized by loss of glycocalyx. In some embodiments, the endothelial dysfunction is characterized by a selectin protein expressed on the surface of endothelial cells and exposed to circulation. In some embodiments, the site suffers from inflammation.

A "disease associated with endothelial dysfunction," as used herein, refers to a human disease or condition that is at least in part caused by endothelial dysfunction or that induces endothelial dysfunction. Treating a disease associated with endothelial dysfunction, accordingly, refers to the treatment of the disease, recovering the dysfunctional endothelium, or preventing or ameliorating conditions or symptoms arising from dysfunctional endothelium, such as inflammation, intimal hyperplasia, and thrombosis.

As disclosed, in some embodiments, the EC-SEAL conjugates can inhibit dysfunctional endothelial cells to treat, inhibit, or attenuate inflammatory diseases. Dysfunctional endothelial cells are associated with inflammation and other inflammatory diseases as evidenced by Ley, "The role of selectins in inflammation and disease", Vol. 9, Elsevier Science, (2003). Examples of other inflammatory diseases and autoimmune diseases include atherosclerosis, coronary artery disease, diabetes mellitus, hypertension, hypercholesterolemia, rheumatoid arthritis, systemic lupus erythematosus, glaucoma, uremia, sepsis, and organ failure.

By inhibiting the production of selectin receptors and masking VCAM/ICAM receptors, the EC-SEAL conjugates can be used to treat patients suffering from these transient or chronic diseases. Evidence of selectin inhibition associated with inhibiting or attenuating these diseases is supported in Ridings et al., "A dual-binding antibody to E- and L-selectin attenuates sepsis-induced lung injury", Vol. 152, American Journal of Respiratory and Critical Care Medicine, (1995), Weyrich et al., "In Vivo Neutralization of P-Selectin Protects Feline Heart and Endothelium in Myocardial Ischemia and Reperfusion Injury", Vol. 91, The American Society for Clinical Investigation, (1993), each of which is incorporated herein by reference. It is known in the art that some cancers are also associated with inflammation and chronic inflammation, and therefore the EC-SEAL conjugates can be used to treat, inhibit, or attenuate neoplastic cell growth.

In an illustrative embodiment, the EC-SEAL conjugates of the present disclosure can be used in vascular intervention procedures including, for example, to prevent any one or a combination of platelet binding to the denuded endothelium, platelet activation, thrombosis, inflammation resulting from denuding the endothelium, intimal hyperplasia, and vasospasm. The EC-SEAL conjugates described herein can also inhibit inflammatory responses by inhibiting the production of selectins or ICAMs/VCAMs in dysfunctional endothelial cells.

Administration and Formulations

The EC-SEAL conjugates described herein can be administered to a patient (e.g., a patient in need of treatment to inhibit platelet activation, such as that involved in thrombosis, platelet binding to denuded endothelium, thrombosis, inflammation resulting from denuding the endothelium, intimal hyperplasia, or vasospasm). In various embodiments, the EC-SEAL conjugates can be administered intravenously or into muscle, for example. Suitable routes for parenteral administration include intravascular, intravenous, intraarterial, intramuscular, cutaneous, subcutaneous, percutaneous, intradermal, and intraepidermal delivery. Suitable means for parenteral administration include needle (including microneedle) injectors, infusion techniques, and catheter-based delivery.

Pharmaceutical compositions of any of the EC-SEAL conjugates described herein can be formulated for parenteral administration or catheter-based delivery. For example, such compositions can include:

a) a pharmaceutically active amount of one or more of the EC-SEAL conjugates;
b) a pharmaceutically acceptable pH buffering agent to provide a pH in the range of about pH 4.5 to about pH 9;
c) an ionic strength modifying agent in the concentration range of about 0 to about 300 millimolar; and
d) water soluble viscosity modifying agent in the concentration range of about 0.25% to about 10% total formula weight or any individual component a), b), c), or d) or any combinations of a), b), c) and d) are provided.

In various embodiments described herein, the pH buffering agents for use in the compositions and methods herein described are those agents known to the skilled artisan and include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES.

In various embodiments described herein, the ionic strength modifying agents include those agents known in the art, for example, glycerin, propylene glycol, mannitol, glucose, dextrose, sorbitol, sodium chloride, potassium chloride, and other electrolytes.

Useful viscosity modulating agents include but are not limited to, ionic and non-ionic water soluble polymers; crosslinked acrylic acid polymers such as the "carbomer" family of polymers, e.g., carboxypolyalkylenes that may be obtained commercially under the Carbopol® trademark; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; gums such as tragacanth and xanthan gum; sodium alginate; gelatin, hyaluronic acid and salts thereof, chitosans, gellans or any combination thereof. Typically, non-acidic viscosity enhancing agents, such as a neutral or basic agent are employed in order to facilitate achieving the desired pH of the formulation.

In various embodiments described herein, parenteral formulations may be suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques available to those skilled in the art.

In various embodiments described herein, the solubility of EC-SEAL conjugates used in the preparation of a parenteral formulation may be increased by the use of appropriate formulation techniques, such as the incorporation of solubility-enhancing compositions such as mannitol, ethanol, glycerin, polyethylene glycols, propylene glycol, poloxomers, and others known to those of skill in the art.

In various embodiments described herein, formulations for parenteral administration may be formulated to be for immediate and/or modified release. Modified release formulations include delayed, sustained, pulsed, controlled, targeted and programmed release formulations. Thus, one or more EC-SEAL conjugates may be formulated as a solid, semi-solid, or thixotropic liquid for administration as an implanted depot providing modified release of the active compound. Illustrative examples of such formulations include drug-coated stents and copolymeric(dl-lactic, glycolic)acid (PGLA) microspheres. In another embodiment, one or more EC-SEAL conjugates, or compositions comprising one or more EC-SEAL conjugates, can be continuously administered, where appropriate.

In any of the embodiments described herein, the EC-SEAL conjugates can be administered intravascularly into the patient (e.g., into an artery or vein) in any suitable way. In various embodiments described herein, the EC-SEAL conjugates can be administered into a vessel of a patient prior to, during, or after vascular intervention. In various embodiments, vascular interventions, such as percutaneous coronary intervention (PCI), can include, for example, stenting, atherectomy, grafting, and angioplasty, such as balloon angioplasty. Illustratively, the vascular intervention can be one which involves temporarily occluding an artery, such as a coronary artery or a vein (e.g., balloon angioplasty), or it can be one which does not involve temporarily occluding an artery or a vein (e.g., non-balloon angioplasty procedures, stenting procedures that do not involve balloon angioplasty, etc.). Illustrative modes of delivery can include a catheter, parenteral administration, a coating on a balloon, through a porous balloon, a coated stent, and any combinations thereof or any other known methods of delivery of drugs during a vascular intervention procedure. In one illustrative embodiment, the target vessel can include a coronary artery, e.g., any blood vessel which supplies blood to the heart tissue of a patient, including native coronary arteries as well as those which have been grafted into the patient, for example, in an earlier coronary artery bypass procedure.

In any of the embodiments described herein, the target vessel into which the EC-SEAL conjugates are to be administered and on which the vascular intervention procedure is to be performed may contain a blockage, such as a stenosis or some other form of complete or partial blockage which causes reduced blood flow through the vessel. Thus, the EC-SEAL conjugates can be delivered to the vessel via a catheter (e.g., a dilatation catheter, an over-the-wire angioplasty balloon catheter, an infusion catheter, a rapid exchange or monorail catheter, or any other catheter device known in the art) which is percutaneously inserted into the patient and which is threaded through the patient's blood vessels to the target vessel. Various catheter-based devices are available in the art, including those described in U.S. Pat. No. 7,300,454, incorporated herein by reference. In various embodiments described herein where a catheter is used, the catheter used to deliver the EC-SEAL conjugates can be the same catheter through which the vascular intervention is to be performed, or it can be a different catheter (e.g., a different catheter which is percutaneously inserted into the patient via the same or a different cutaneous incision and/or which is threaded through the patient's blood vessels to the target vessel via the same or a different route). In another embodiment, the EC-SEAL conjugates can be injected directly into the target vessel. In another embodiment, the EC-SEAL conjugates can be delivered systemically (i.e., not delivered directly to the target vessel, but delivered by parenteral administration without catheter-based delivery).

In the case where the vessel contains a blockage (e.g., a stenosis), administration can be carried out by delivering the EC-SEAL conjugates directly to the target vessel at the site of the blockage or distal to the blockage or both. In another embodiment, the EC-SEAL conjugates can be delivered to one or more sites proximal to the blockage. Illustratively, the catheter tip can be maintained stationary while EC-SEAL conjugates are being delivered, or the catheter tip can be moved while the EC-SEAL conjugates are being delivered (e.g., in a proximal direction from a position that is initially distal to the blockage, to or through the blockage, or to a position which is proximal to the blockage).

As indicated above, EC-SEAL conjugates can be administered directly into the patient's vessel at a time prior to vascular intervention, e.g., percutaneous coronary intervention. For example, delivery of the EC-SEAL conjugates can be carried out just prior to vascular intervention (e.g., within about 1 hour, such as within about 30 minutes, within about 15 minutes, and/or within about 5 minutes prior to vascular intervention). Optionally, delivery of EC-SEAL conjugates directly to the target vessel can be continued during all or part of the vascular intervention procedure and/or subsequent to completion of such procedure, or delivery of the EC-SEAL conjugates directly to the target vessel can be stopped prior to the commencement of the vascular intervention procedure and not subsequently re-commenced. In any of the embodiments described herein, delivery of the EC-SEAL conjugates can be continuous or it can be effected through a single or multiple administrations. Prior to, during, and/or after the EC-SEAL conjugates are administered to the target vessel, the same EC-SEAL conjugates or one or more different EC-SEAL conjugates can be administered.

In any of the embodiments described herein, the EC-SEAL conjugates can be administered alone or in combination with suitable pharmaceutical carriers or diluents. Diluent or carrier ingredients used in the EC-SEAL conjugate formulation can be selected so that they do not diminish the desired effects of the EC-SEAL conjugates. The EC-SEAL conjugate formulation may be in any suitable form. Examples of suitable dosage forms include aqueous solutions of the EC-SEAL conjugates, for example, a solution in isotonic saline, 5% glucose or other well-known pharmaceutically acceptable liquid carriers such as alcohols, glycols, esters and amides.

Suitable dosages of the EC-SEAL conjugates can be determined by standard methods, for example by establishing dose-response curves in laboratory animal models or in clinical trials. Illustratively, suitable dosages of EC-SEAL conjugates (administered in a single bolus or over time) include from 1 ng/kg to about 10 mg/kg, 100 ng/kg to about 1 mg/kg, from about 1 µg/kg to about 500 µg/kg, or from about 100 µg/kg to about 400 µg/kg. In each of these embodiments, dose/kg refers to the dose per kilogram of patient mass or body weight. In other illustrative aspects, effective doses can range from about 0.01 µg to about 1000 mg per dose, 1 µg to about 100 mg per dose, or from about 100 µg to about 50 mg per dose, or from about 500 µg to about 10 mg per dose or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose.

Vascular intervention, such as percutaneous coronary intervention, can be carried out by any conventional procedure prior to, during, or after administration of the EC-SEAL conjugates. Examples of vascular intervention procedures contemplated for use in conjunction with the methods of the present disclosure include stenting, atherectomy, and angioplasty, such as balloon angioplasty. The vascular intervention procedure can be one which involves temporarily occluding the vessel (e.g., balloon angioplasty), or it can be one which does not involve temporarily occluding the vessel (e.g., non-balloon angioplasty procedures, stenting procedures that do not involve balloon angioplasty, etc.). Illustrative modes of delivery can include a catheter, parenteral administration, a coating on a balloon, through a porous balloon, a coated stent, and any combinations thereof or any other known methods of delivery of drugs during a vascular intervention procedure.

It is also contemplated that any of the formulations described herein may be used to administer the EC-SEAL conjugates (e.g., one or more types) either in the absence or the presence of a catheter-based device. The EC-SEAL conjugates can be formulated in an excipient. In any of the embodiments described herein, the excipient can have a concentration ranging from about 0.4 mg/ml to about 6 mg/ml. In various embodiments, the concentration of the excipient may range from about 0.5 mg/ml to about 10 mg/ml, about 0.1 mg/ml to about 6 mg/ml, about 0.5 mg/ml to about 3 mg/ml, about 1 mg/ml to about 3 mg/ml, about 0.01 mg/ml to about 10 mg/ml, and about 2 mg/ml to about 4 mg/ml.

The dosage of the EC-SEAL conjugates can vary significantly depending on the patient condition, the disease state being treated, the route of administration and tissue distribution, and the possibility of co-usage of other therapeutic treatments. The effective amount to be administered to a patient is based on body surface area, patient weight or mass, and physician assessment of patient condition. In various exemplary embodiments, an effective dose can range from about 1 ng/kg to about 10 mg/kg, 100 ng/kg to about 1 mg/kg, from about 1 µg/kg to about 500 µg/kg, or from about 100 µg/kg to about 400 µg/kg. In each of these embodiments, dose/kg refers to the dose per kilogram of patient mass or body weight. In other illustrative aspects, effective doses can range from about 0.01 µg to about 1000 mg per dose, 1 µg to about 100 mg per dose, or from about 100 µg to about 50 mg per dose, or from about 500 µg to about 10 mg per dose or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose. In any of the various embodiments described herein, effective doses can range from about 0.01 µg to about 1000 mg per dose, 1 µg to about 100 mg per dose, about 100 µg to about 1.0 mg, about 50 µg to about 600 µg, about 50 µg to about 700 about 100 µg to about 200 about 100 µg to about 600 about 100 µg to about 500 about 200 µg to about 600 µg, or from about 100 µg to about 50 mg per dose, or from about 500 µg to about 10 mg per dose or from about 1 mg to 10 mg per dose. In other illustrative embodiments, effective doses can be 1 µg, 10 µg, 25 µg, 50 µg, 75 µg, 100 µg, 125 µg, 150 µg, 200 µg, 250 µg, 275 µg, 300 µg, 350 µg, 400 µg, 450 µg, 500 µg, 550 µg, 575 µg, 600 µg, 625 µg, 650 µg, 675 µg, 700 µg, 800 µg, 900 µg, 1.0 mg, 1.5 mg, 2.0 mg, 10 mg, 100 mg, or 100 mg to 30 grams.

Any effective regimen for administering the EC-SEAL conjugates can be used. For example, the EC-SEAL conjugates can be administered as a single dose, or as a multiple-dose daily regimen. Further, a staggered regimen, for example, one to five days per week can be used as an alternative to daily treatment.

In certain embodiments, mixed micelles can also be formulated that include collagen binding peptidoglycans (e.g., the DS-SILY conjugates described in US 2013/0190246) combined with one or more types of the EC-SEAL conjugates described herein. The DS-SILY and EC-SEAL conjugates can both have alkyl tails, and therefore by combining DS-SILY-tail:EC-SEAL-tail (e.g., 1:1) mixed micelles are generated bind to endothelium, or to exposed ICAM, VCAM, selectin, and/or collagen. The alkyl tail structures can be optimized for micelle formation and for dissociation of the micelles over time.

In various embodiments described herein, the patient is treated with multiple injections of the EC-SEAL conjugates. In one embodiment, the patient is injected multiple times (e.g., about 2 up to about 50 times) with the EC-SEAL conjugates, for example, at 12-72 hour intervals or at 48-72 hour intervals. Additional injections of the EC-SEAL conjugates can be administered to the patient at an interval of days or months after the initial injections(s).

In any of the embodiments herein described, it is to be understood that a combination of two or more EC-SEAL conjugates, differing in the peptide portion, the glycan portion, or both, can be used in place of a single EC-SEAL conjugate.

It is also appreciated that in the foregoing embodiments, certain aspects of the compounds, compositions and methods are presented in the alternative in lists, such as, illustratively, selections for any one or more of GAG and peptide. It is therefore to be understood that various alternate embodiments of the disclosure include individual members of those lists, as well as the various subsets of those lists. Each of those combinations is to be understood to be described herein by way of the lists.

EC-SEAL conjugates can be sterilized before, during and/or after formulation. As used herein "sterilization" or "sterilize" or "sterilized" means disinfecting the EC-SEAL conjugates by removing unwanted contaminants including, but not limited to, endotoxins and infectious agents.

In various illustrative embodiments, the EC-SEAL conjugates can be disinfected and/or sterilized using conventional sterilization techniques including propylene oxide or ethylene oxide treatment, gas plasma sterilization, gamma radiation, electron beam, and/or sterilization with a peracid, such as peracetic acid. Sterilization techniques which do not adversely affect the structure and biotropic properties of the EC-SEAL conjugates can be used. Illustrative sterilization techniques include exposing the EC-SEAL conjugates to peracetic acid, 1-4 Mrads gamma irradiation (or 1-2.5 Mrads of gamma irradiation), ethylene oxide treatment, sterile filtration, or gas plasma sterilization. In one embodiment, the EC-SEAL conjugates can be subjected to one or more sterilization processes. For example, the EC-SEAL conjugates can be subjected to sterile filtration. The EC-SEAL conjugates may dispensed into any type of container, which can be wrapped in a plastic wrap or a foil wrap, and can be further sterilized after such placement in a container.

The EC-SEAL conjugates can be combined with minerals, amino acids, sugars, peptides, proteins, vitamins (such as ascorbic acid), laminin, collagen, fibronectin, hyaluronic acid, fibrin, elastin, aggrecan, growth factors (such as epidermal growth factor, platelet-derived growth factor, transforming growth factor beta, or fibroblast growth factor), glucocorticoids such as dexamethasone, viscoelastic altering agents such as ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents both natural and synthetic.

Kits

The EC-SEAL conjugates can be provided in one or more types of kits. The kit can include packaging with one or more containers, at least one of which contains an EC-SEAL conjugate. The kit can also contain instructions for use of the components of the kit. In one embodiment, the kit comprises one or more vessels, vials, or containers that hold one or more EC-SEAL conjugates. The kit can also include any of the following components: one or more formulations or concentrations (dosages) of EC-SEAL conjugates, a buffer, a sterilizing or disinfecting agent, a syringe, a needle, proteins or polysaccharides, and/or instructional materials describing methods for using the kit reagents. In any of these embodiments, the kit can contain a component selected from the group consisting of a catheter, a stent, a balloon, and a combination thereof. The EC-SEAL conjugates can be lyophilized, for example, in a buffer or in water.

In any of the embodiments herein described, kits for carrying out vascular intervention, such as the kits described above, are contemplated. The kits can include a catheter or a stent and one or more EC-SEAL conjugates. The EC-SEAL conjugates can be provided in any of the formulations discussed above and in an amount needed to carry out a single vascular intervention, such as from 1 ng/kg to about 10 mg/kg, 100 ng/kg to about 1 mg/kg, from about 1 µg/kg to about 500 µg/kg, or from about 100 µg/kg to about 400 µg/kg. In each of these embodiments, dose/kg refers to the dose per kilogram of patient mass or body weight. In various embodiments herein described, effective doses provided in the formulations can range from about 0.01 µg to about 1000 mg per dose, 1 µg to about 100 mg per dose, or from about 100 µg to about 50 mg per dose, or from about 500 µg to about 10 mg per dose or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose.

Articles of manufacture are also contemplated for any of these embodiments. In any of the kit or article of manufacture embodiments described herein, the kit or article of manufacture can comprise a dose or multiple doses of the EC-SEAL conjugates. The EC-SEAL conjugates can be in a primary container, for example, a glass vial, such as an amber glass vial with a rubber stopper and/or an aluminum tear-off seal. In another embodiment, the primary container can be plastic or aluminum, and the primary container can be sealed. In another embodiment, the primary container may be contained within a secondary container to further protect the composition from light.

In any of the embodiments described herein, the kit or article of manufacture can contain instructions for use. Other suitable kit or article of manufacture components include excipients, disintegrants, binders, salts, local anesthetics (e.g., lidocaine), diluents, preservatives, chelating agents, buffers, tonicity agents, antiseptic agents, wetting agents, emulsifiers, dispersants, stabilizers, and the like. These components may be available separately or admixed with the EC-SEAL conjugates. Any of the composition embodiments described herein can be used to formulate the kit or article of manufacture.

In various embodiments herein described, the kit can contain more than one catheter or a stent and a plurality of separate containers, each containing sterilized EC-SEAL conjugate formulations in an amount needed to carry out a single or multiple vascular interventions. Any type of stent or catheter may be included with the kit, including, for example, dilatation catheters, over-the-wire angioplasty balloon catheters, infusion catheters, rapid exchange or monorail catheters, and the like.

The following are alternative embodiments.

1. An EC-SEAL conjugate comprising a peptide ligand, a glycosaminoglycan, and an optional alkyl tail.
2. The EC-SEAL conjugate of statement 1, comprising a structure of the following formula:

a. Alkyl-GAG(P)n.

b. wherein: Alkyl is a $C_{2-18}$ alkyl chain;
      1. GAG is a glycosaminoglycan such as alginate, agarose, dextran, dextran sulfate, chondroitin, chondroitin sulfate, dermatan, dermatan sulfate, heparin, heparan sulfate, keratin, keratan sulfate, hyaluronan, or a combination thereof;
      2. P is a peptide of 5 to about 40 amino acids that can bind to a selectin, and ICAM or a VCAM; and
      3. n is an integer of 3-50.
3. The EC-SEAL conjugate of statement 1 or 2, wherein the glycosaminoglycan (e.g., the GAG group) is heparin, chondroitin sulfate and heparan sulfate.
4. The EC-SEAL conjugate of any of statements 1-3, wherein the EC-SEAL conjugate binds to endothelial cells.
5. The EC-SEAL conjugate of any of statements 1-4, wherein the EC-SEAL conjugate binds to endothelial tissue in a blood vessel of a mammal.
6. The EC-SEAL conjugate of any of statements 1-5, wherein the EC-SEAL conjugate inhibits platelet activation, inhibits platelet binding to a mammalian blood vessel, inhibits intimal hyperplasia, inflammation in a mammalian blood vessel, inhibits thrombosis, inhibits vasospasm, stimulates endothelial cell proliferation, binds to exposed selectin, ICAM, VCAM, or combinations thereof in a mammalian blood vessel.
7. The EC-SEAL conjugate of any of statements 1-6, wherein the EC-SEAL conjugate inhibits or reduces the incidence of arteriovenous fistulae failure in a hemolysis patient.
8. The EC-SEAL conjugate of any of statements 1-7, wherein the EC-SEAL conjugate has an alkyl tail (e.g., the Alkyl group) that is a $C_{3-16}$ alkyl chain, or a $C_{4-15}$ alkyl chain, or a $C_{5-14}$ alkyl chain, or a $C_{3-12}$ alkyl chain.
9. The EC-SEAL conjugate of any of statements 1-8, wherein the glycosaminoglycan (e.g., the GAG group) is dermatan sulfate, dextran, hyaluronan, heparin or a combination thereof.
10. The EC-SEAL conjugate of any of statements 1-9, wherein the glycosaminoglycan (e.g., the GAG group) is dermatan sulfate.
11. The EC-SEAL conjugate of any of statements 1-10, wherein peptide ligand (e.g., the P group) is a peptide of 5 to about 35 amino acids, or a peptide of 5 to about 30 amino acids, or peptide of 5 to about 25 amino acids.
12. The EC-SEAL conjugate of any of statements 1-11, wherein the peptide ligand is a peptide with at least 80% sequence identity to any of IELLQAR (SEQ ID NO: 1); IELLQARGSC (SEQ ID NO: 2); IDLMQAR (SEQ ID NO: 3); IDLMQARGSC (SEQ ID NO: 4); QITWAQLWNMMK (SEQ ID NO: 5); QITWAQLWNMMKGSC (SEQ ID NO: 6), NAFKILVVITFGEK (SEQ ID NO: 7); NAFKILVVITFGEKGSC (SEQ ID NO: 8); ITDGEA (SEQ ID NO: 9); ITDGEAGSC (SEQ ID NO: 10); DGEATD (SEQ ID NO: 11); or DGEATDGSC (SEQ ID NO: 12).

13. The EC-SEAL conjugate of any of statements 1-12, wherein the peptide ligand is a peptide with at least 80%, or at least 85%, or at least 90%, or at least 95% sequence identity to any of IELLQAR (SEQ ID NO: 1); IELLQARGSC (SEQ ID NO: 2); IDLMQAR (SEQ ID NO: 3); IDLMQARGSC (SEQ ID NO: 4); QITWAQLWNMMK (SEQ ID NO: 5); QITWAQLWNMMKGSC (SEQ ID NO: 6), NAFKILVVITFGEK (SEQ ID NO: 7); NAFKILVVITFGEKGSC (SEQ ID NO: 8); ITDGEA (SEQ ID NO: 9); ITDGEAGSC (SEQ ID NO: 10); DGEATD (SEQ ID NO: 11); or DGEATDGSC (SEQ ID NO: 12).
14. The EC-SEAL conjugate of any of statements 1-13, wherein the peptide ligand is linked to the glycosaminoglycan via a crosslinker.
15. A composition comprising the EC-SEAL conjugate of any of statements 1-14.
16. The composition of statement 15, comprising an excipient or carrier.
17. The composition of statement 15 or 16, comprising a pharmaceutically acceptable excipient or carrier.
18. The composition of any of statements 15-17, formulated for parenteral, intravascular, intravenous, intraarterial, intramuscular, cutaneous, subcutaneous, percutaneous, intradermal, and/or intraepidermal administration.
19. The composition of any of statements 15-18, formulated for parenteral administration using a needle or a device for infusion.
20. The composition of any of statements 15-19, formulated for administration to a mammal via a catheter, as a coating on a balloon, through a porous balloon, or as a coating on a stent.
21. A method for vascular intervention comprising: administering the EC-SEAL conjugate of any of statements 1-14, or the composition of any of statements 15-20. to a mammal during or after the vascular intervention.
22. The method of statement 21, wherein the EC-SEAL conjugate binds to a endothelial tissues in a blood vessel of the mammal.
23. The method of statement 21 or 22, wherein the EC-SEAL conjugate ameliorates endothelial dysfunction.
24. The method of any of statements 21-23, wherein the EC-SEAL conjugate inhibits platelet activation, inhibits platelet binding to a mammalian blood vessel, inhibits intimal hyperplasia, inflammation in a mammalian blood vessel, inhibits thrombosis, inhibits vasospasm, stimulates endothelial cell proliferation, binds to exposed selectin, ICAM, VCAM, or combinations thereof in a mammalian blood vessel.
25. The method of any of statements 21-24, wherein the EC-SEAL conjugate inhibits or reduces the incidence of arteriovenous fistulae failure in a hemolysis patient.
26. A kit comprising the EC-SEAL conjugate of any of statements 1-14, or the composition of any of statements 15-20, and instructions for using the EC-SEAL conjugate or the composition.
27. The kit of statement 26, further comprising a buffer, a sterilizing or disinfecting agent, a syringe, a needle, proteins or polysaccharides, a catheter, a stent, a balloon, and a combination thereof.

The following non-limiting Examples illustrate development of aspects of the disclosure.

EXAMPLES

Example 1

Selectin and ICAM Binding Peptide Conjugates

Three selectin-binding peptides and three ICAM-binding peptides were selected for development of the EC-SEAL molecules. The selection of peptides was based on the following criteria:

1) Hydrophilicity, which can facilitate the coupling chemistry used to synthesize the conjugate molecules, and to ensure that the final product is soluble in aqueous solutions including blood;

2) Availability of cysteine thiols to couple to the functionalized glycosaminoglycan; and 3) Relative binding affinity for the primary target.

The peptides in Table 2 were selected for investigation and potential development the EC-SEAL molecules.

TABLE 2

Selectin and ICAM targeting peptide sequences

| Target | Peptide Sequence* | $IC_{50}$ |
|---|---|---|
| Selectin# | IELLQAR (SEQ ID NO: 1) | $\sim 2 \times 10^{-4}$ Fukuda et al., Cancer Res 60: 450-6 (2000) |
| Selectin# | IDLMQAR (SEQ ID NO: 3) | $\sim 2 \times 10^{-4}$ Fukuda et al., Cancer Res 60: 450-6 (2000) |
| Selectin# | QITWAQLWNMMK (SEQ ID NO: 5) | $\sim 16 \times 10^{-8}$ Martens et al., J Biol Chem 270: 21129-36 (1995) |
| ICAM | NAFKILVVITFGEK (SEQ ID NO: 7) | Unknown Kalstad et al., Engineering in Medicine and Biology, 2002 24th Annual Conference and the Annual Fall Meeting of the Biomedical Engineering Society EMBS/BMES Conference, 2002 Proceedings of the Second |

TABLE 2-continued

Selectin and ICAM targeting peptide sequences

| Target | Peptide Sequence* | IC$_{50}$ |
|---|---|---|
| | | Joint. p. 736-7 vol.1 (2002); Feng et al., J Biol Chem 273: 5625-30 (1998). |
| ICAM | ITDGEA (SEQ ID NO: 9) | Unknown Yusuf-Makagiansar et al., Chem. Biol, & Drug Design 70: 237-46 (2007). |
| ICAM | DGEATD (SEQ ID NO: 11) | Unknown Yusuf-Makagiansar et al., Chem. Biol, & Drug Design 70: 237-46 (2007). |

*the amino acids GSC will be added to the C-terminus of each peptide for conjugation.
peptide binds to both E-Selectin and S-Selectin.

Example 2

Selectin-Binding EC-SEAL Binds to Endothelial Cells

This Example describes a first generation EC-SEAL molecule that includes a peptide that binds to selectin conjugated to dermatan sulfate, as well as illustrating the binding of this EC-SEAL molecule to endothelial cells.

Methods

Peptidoglycan Synthesis: Dermatan sulfate (DS) was oxidized by periodate oxidation in which the degree of oxidation was controlled by varying amounts of sodium metaperiodate. After oxidizing at room temperature for 2 hours protected from light, the oxidized dermatan sulfate was desalted into 1×PBS pH 7.2 by size exclusion chromatography using a column packed with Bio-gel P-6 (BioRad). The heterobifunctional crosslinker 3-maleimidopropionic acid hydrazide (BMPH) was added to oxidized dermatan sulfate in 30 fold molar excess over the amount of dermatan sulfate, and the reaction mixture was reacted for 4 hours at room temperature while protected from light. The intermediate dermatan sulfate-crosslinker product was then purified of excess crosslinker by size exclusion chromatography using a Bio-gel P-6 column and 1×PBS pH 7.2 as running buffer. The number of crosslinkers attached to dermatan sulfate was calculated by the consumption of crosslinker determined from the 215 nm crosslinker peak area, determined spectroscopically with use of a standard curve of crosslinker concentration versus absorption.

The free peptide IELLQARGC (SEQ ID NO: 105); sometimes referred to as QAR) was dissolved into dimethylformamide (DMF) at a concentration of 10 mg/mL and was added in 1 molar excess to the number of attached crosslinkers. The reaction mixture was incubated for 2 hours at room temperature. The final product DS-QAR$_n$ was purified by size exclusion chromatography using a Bio-gel P-6 column with Millipore water as the running buffer. The final product was immediately frozen, lyophilized, and stored at −20 C until further testing.

A biotin labeled version of the peptidoglycan was also synthesized by reacting 1 mole of QAR$_{biotin}$ per mole of DS-BMPH for 1 h, followed by addition of unlabeled QAR to complete the reaction and form DS-QAR$_{n\text{-}biotin}$.

Cell Culture: Human aortic endothelial cells (HAEC) (Invitrogen) were cultured in growth medium (Medium 200 supplemented with low serum growth supplement; Invitrogen). Cells from passages 3-5 were used for all experiments. Growth medium was used for all experiments unless otherwise noted.

Binding of DS-QAR to HAECs: HAECs were seeded at $1\times10^5$ cells/cm$^2$ in growth medium on to Ibidi angiogenesis (Ibidi) and allowed to adhere for 24 hrs. Growth medium was aspirated and cells were incubated in growth medium containing 1 ng/mL tumor necrosis factor-α (TNF-α) for 4 hrs. TNF-α-stimulated medium was aspirated and 50 μM EC-SEAL$_{20\text{-}biotin}$ in Tris buffered saline (TB S) with 150 mM calcium chloride was added to each well. Cells were incubated for 15 min at 37° C. and rinsed 3 times with TBS. Cells were then blocked with 1% BSA in TBS for 30 minutes at room temperature. Cell nuclei were stained using 1 μg/mL SYTOX green (Invitrogen) for 10 min. Plates were rinsed 3 times with TBS containing 1% BSA. EC-SEAL$_{20\text{-}biotin}$ was detected using streptavidin-Dylight 633 (Thermo Scientific). Plates were rinsed 3 times with TBS containing 1% BSA bef. Cells were visualized using an Olympus FV1000 confocal microscope with 60× objective. Cells lacking TNF-α stimulation were used as control.

Results

Oxidized dermatan sulfate (DS, MW 60 KDa) was employed as the scaffold for attachment of an average of 20 selectin-binding peptides (each with the sequence IELLQAR, SEQ ID NO: 106) to each dermatan sulfate molecule. Such a construct was the first generation EC-SEAL molecule tested.

To evaluate the binding of this first generation EC-SEAL molecule, human aortic endothelial cells were exposed to 5 ng/ml TNFα for 4 hours to induce inflammation and upregulation of E- and P-selectin, then the cells were treated with 2 mg/ml biotin-EC-SEAL for 1 hour. As a control, some human coronary endothelial cells were exposed to an equivalent volume of PBS for 4 hours, and then treated with 2 mg/ml biotin-EC-SEAL for 1 hour. After such treatment, the cells were rinsed, fixed and probed with avidin-alexafluor.

FIG. 1A shows images of the TNFα stimulated endothelial cells (nuclei-green) with bound EC-SEAL molecules (in red, with yellow arrows pointing to the EC-SEAL surrounding some cells). FIG. 1B shows images of PBS stimulated endothelial cells treated with EC-SEAL, showing that little or no EC-SEAL molecules are bound when no inflammation and upregulation of E-selectin and P-selectin are induced.

Thus, the first generation EC-SEAL bound to these human aortic cells, but not to endothelial cells cultured in the absence of TNF-α (FIG. 1).

Example 3

Optimal Ratios of Peptide to Glycosaminoglycan Scaffold

This Example describes experiments that can be used to evaluate the optimal ratio of peptide ligand to glycosaminoglycan (GAG) scaffold molecule.

To determine peptide identity and optimal peptide ratios per GAG, the number of peptides per backbone is first examined and then the different ratios of selectin-vs. ICAM-binding peptides are evaluated.

Different conjugate molecules are generated for each selectin-binding peptide and each ICAM-binding peptide using dermatan sulfate as the backbone for conjugates. Conjugate molecules were prepared with a dermatan sulfate backbone and 10, 15, 20, or 30 peptides per backbone of just one type of selectin-binding peptide or just one type of ICAM-binding peptide. Each molecule will also contain on average one peptide labeled with a biotin tag for monitoring presence of the molecules as described by Paderi et al., Biomaterials 32:2516-23 (2011).

HUVEC cells can be used to evaluate the degree of coverage on TNF-α-activated and unactivated endothelial cells. TNF-α activates E-selectin and ICAM synthesis (Sakhalkar et al., Proc. Nat'l. Acad. Sci. 100:15895-900 (2003)). TNF-α-activated and unactivated endothelial cells are separately mixed with a selected peptide conjugate. The extent of cell coverage is monitored at 4 hours and then daily for 7 days for those conjugates that bind to the activated endothelial cells but not the unactivated endothelial cells. Media will be changed every other day with continued TNF-α stimulation. Coverage of the cells by the peptide conjugates can be assessed in two ways. First, cell coverage can be evaluated by staining with fluorescent avidin. Second, the binding of cells such as HL60 cells that would normally bind to activated endothelium can be evaluated (Fukuda et al., Cancer Res 60:450-6 (2000)). Endothelial cell cultures can be challenged with leukocyte cell line HL60 and inhibition of HL60 binding to the activated endothelium can be evaluated. Cytokine secretion can be assessed using the Meso Scale Discovery (MSD) as described by Scott et al., PloS one 8:e82456 (2013)). Decreased cytokine secretion is an indicator of decreased inflammation Butterfield et al., Biochemistry 49:1549-55 (2010)).

The following EC-SEAL conjugates (peptide conjugates) have been synthesized and tested as described above.

| GAG | Peptide | Average number of peptides per GAG | Abbreviation |
|---|---|---|---|
| DS | IDLMQARGC (SEQ ID NO: 107) | 10 | IDL-10 |
| DS | IDLMQARGC (SEQ ID NO: 107) | 15 | IDL-15 |
| DS | IDLMQARGC (SEQ ID NO: 107) | 20 | IDL-20 |
| DS | IDLMQARGC (SEQ ID NO: 107) | 30 | IDL-30 |
| DS | IELLQARGC (SEQ ID NO: 108) | 10 | IEL-10 |
| DS | IELLQARGC (SEQ ID NO: 108) | 15 | IEL-15 |
| DS | IELLQARGC (SEQ ID NO: 108) | 20 | IEL-20 |
| DS | IELLQARGC (SEQ ID NO: 108) | 30 | IEL-30 |
| DS | QITWAQLWMMKGC (SEQ ID NO: 109) | 10 | QIT-10 |
| DS | QITWAQLWMMKGC (SEQ ID NO: 109) | 15 | QIT-15 |
| DS | QITWAQLWMMKGC (SEQ ID NO: 109) | 20 | QIT-20 |
| DS | QITWAQLWMMKGC (SEQ ID NO: 109) | 30 | QIT-30 |
| DS | DGEATDGC (SEQ ID NO: 110) | 10 | DGE-10 |
| DS | DGEATDGC (SEQ ID NO: 110) | 15 | DGE-15 |
| DS | DGEATDGC (SEQ ID NO: 110) | 20 | DGE-20 |
| DS | DGEATDGC (SEQ ID NO: 110) | 30 | DGE-30 |
| DS | ITDGEAGC (SEQ ID NO: 114) | 10 | ITD-10 |
| DS | ITDGEAGC (SEQ ID NO: 114) | 15 | ITD-15 |
| DS | ITDGEAGC (SEQ ID NO: 114) | 20 | ITD-20 |
| DS | ITDGEAGC (SEQ ID NO: 114) | 30 | ITD-30 |

*each peptide included the GC for conjugation to the DS.

In the above table, DS stands for dermatan sulfate, IDL (IDLMQARGC (SEQ ID NO: 107)), IEL (IELLQARGC (SEQ ID NO: 108)) and QIT (QITWAQLWMMKGC (SEQ ID NO: 109)) are selectin-binding peptides and ITD (ITDGEAGC SEQ ID NO: 114) and DGE (DGEATDGC (SEQ ID NO: 110)) are intracellular adhesions molecule (ICAM)-binding peptides. Each molecule contains, on average, one biotinylated peptide for labeling purposes.

To determine relative binding affinity of each EC-SEAL conjugate to endothelial cells (ECs), ECs were seeded to form a monolayer in 96-well plates. Cultures were then stimulated with 5 ng/mL tumor necrosis factor-α (TNF-α) in cell culture medium for 4 hours. Following removal of medium, cells were treated for 1 hour with tris buffered saline (TB S) with 150 mM calcium chloride ('control') or 30 μM of each variant of EC-SEAL in TBS with 150 mM calcium chloride ('ABC-##'). Treatments were removed, cells were rinsed and Streptavidin-HRP (1:200 in 1% bovine serum albumin (BSA) in TBS) was added to each well and incubated at room temperature for 20 minutes. Following rinsing, a substrate solution of color reagents was added to each well (1:1 hydrogen peroxide: tetramethylbenzidine) and again, incubated at room temperature for 20 minutes. Final reaction was stopped using 2N sulfuric acid ($H_2SO_4$) and absorbance was read on an M5 Plate Reader at 450 nm and 540 nm.

Figure 2:
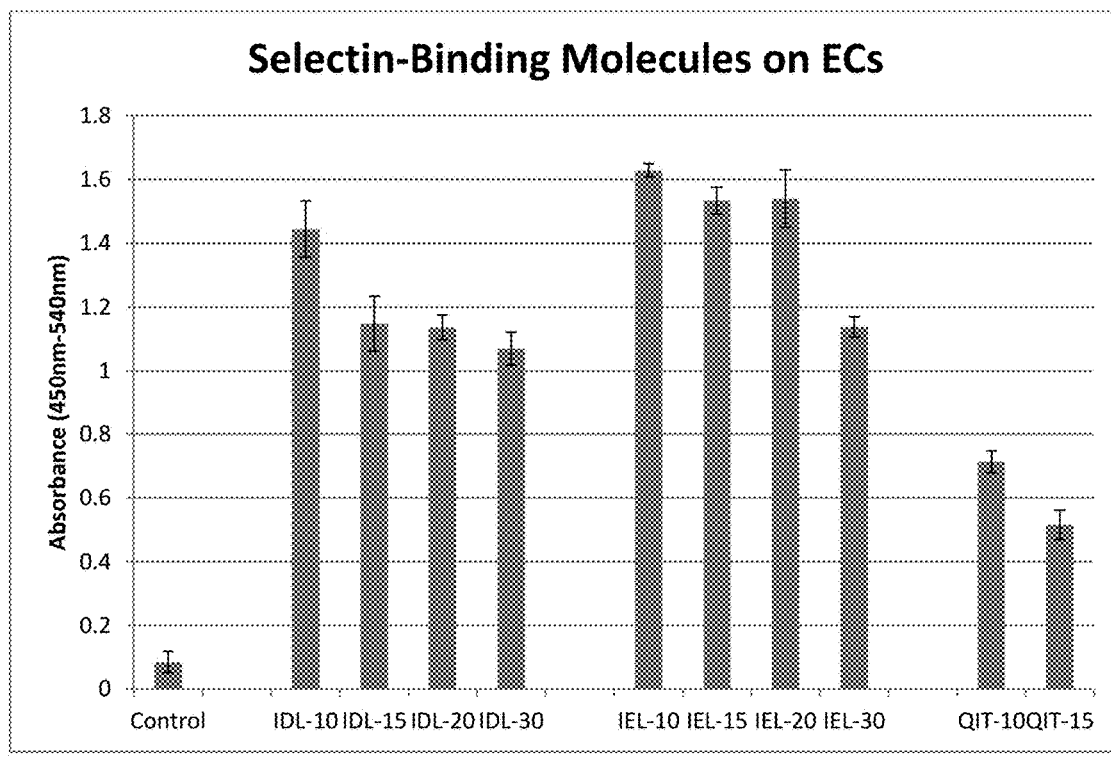
FIG. 2 shows the relative binding affinities of selectin-binding EC-SEAL conjugates on endothelial cells (ECs).
Figure 3:
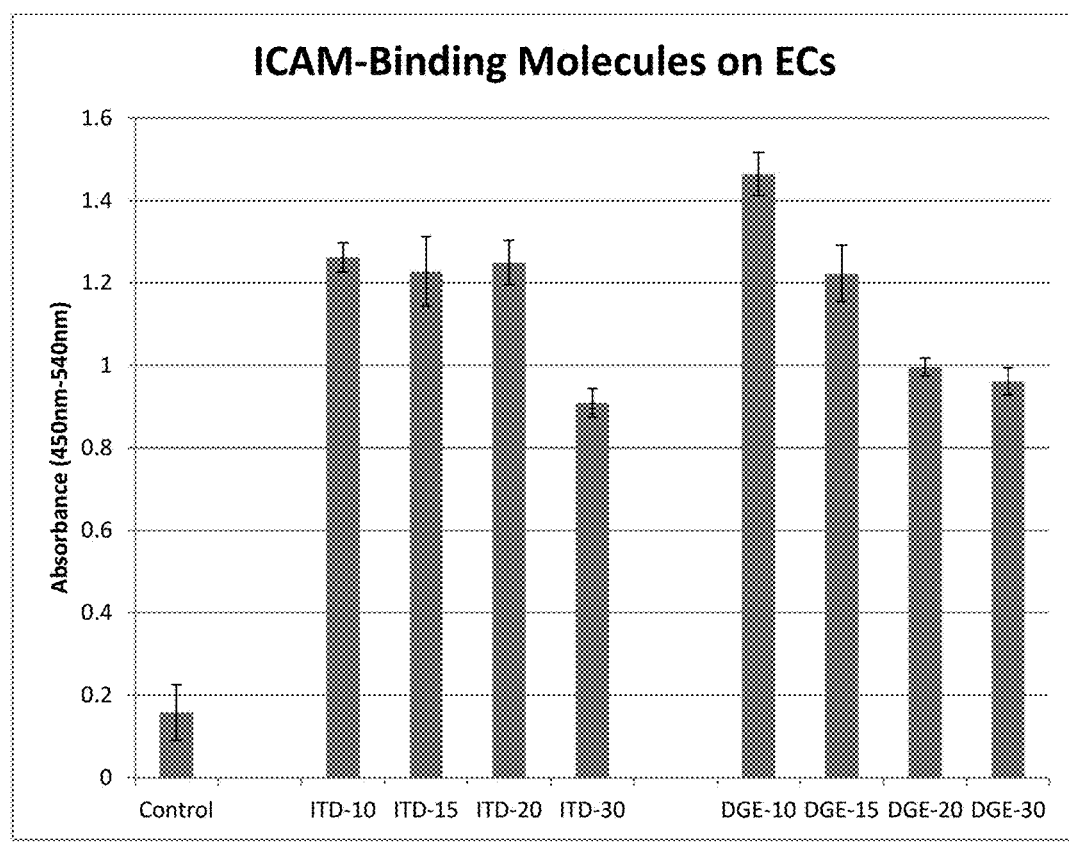
FIG. 3 shows the relative binding affinities of ICAM-Binding EC-SEAL conjugates on endothelial cells (ECs).
Figure 4:
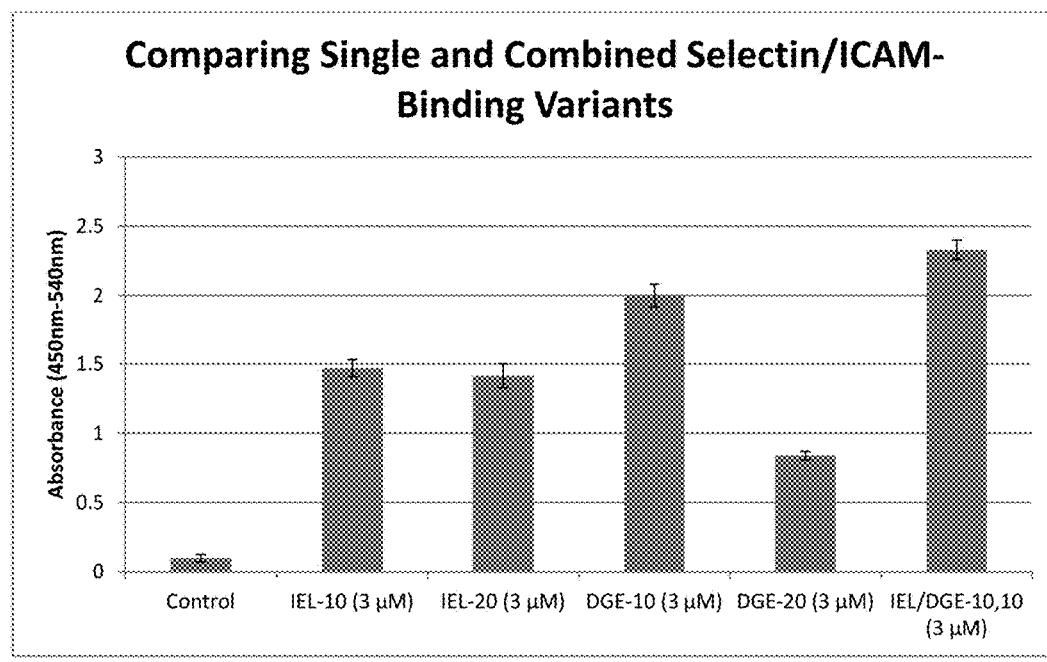
FIG. 4 shows the relative binding affinities of single selectin or ICAM-binding EC-SEAL conjugates and EC- SEAL conjugates having both selectin and ICAM-binding peptides on endothelial cells (ECs).

FIGS. 2 and 3 show the endothelial cell-binding experiment results for EC-SEAL conjugates as described above. These results indicate that the EC-SEAL conjugates are indeed binding to the ECs and that each peptide group (and the variants within each peptide group) has varying binding affinities to the TNF-α stimulated cells. Specifically, IEL (selectin-binding) and DGE (ICAM-binding) seem to exhibit the best binding, while QIT (selectin-binding) appears to have the least. Also of note is that treatments with 30 peptides per DS molecule tend to have decreased binding affinities in all peptide groups.

It has been contemplated that targeting both selectin and ICAM receptors will increase binding affinity, therefore an EC-SEAL conjugate having both selectin and ICAM-binding peptides was synthesized using dermatan sulfate (DS) and tested. The EC-SEAL conjugate had an average of about ten IEL (IELLQARGC (SEQ ID NO: 108)) peptides and an average of about ten DGE (DGEATDGC (SEQ ID NO: 110)) peptides per DS. The EC-SEAL conjugate (abbreviated as IEL/DGE-10,10) was tested to determine binding to ECs as compared to single receptor-binding peptide EC-SEAL conjugates. Cell seeding and stimulation were done as previously described and 3 μM treatments were applied to determine relative binding affinities (FIG. 4). These results indicate that the combined selectin/ICAM-binding molecule indeed exhibit a greater binding to ECs than the respective single selectin or ICAM-binding variants having a total of about peptide ligands per GAG.

Example 4

Formulation and Delivery Methods for EC-SEAL

This Example describes methods to facilitate cell coating with the EC-SEAL conjugates described herein in the event of increased endothelial cell activation. Nanoparticles of EC-SEAL conjugates can be employed that will slowly dissociate in vivo to deliver additional free EC-SEAL to the lumen of a vessel.

Methods to end-functionalize DS with aliphatic tails to induce micelle formation are described below. All GAGs have a reducing end, to which facile conjugation can be achieved. We will take advantage of conjugation at the reducing end to develop micelles that dissociate over ~48 hours in vivo. These micelles are designed to bind to exposed endothelial tissues and release additional EC-SEAL over the first 48 hours. The micelles provide additional EC-SEAL to coat newly denuded areas in case of additional endothelial cell activation or loss and to coat endothelial cells that upregulate selectins and ICAM at later time points.

Micelle Synthesis: To add amine functionality to the reducing end of the DS, the DS will be incubated in a saturated solution of ammonium bicarbonate at room temperature for 4-5 hours followed by extended lyophilization to remove the unreacted ammonium bicarbonate as we have done previously (Butterfield et al., Biochemistry 49:1549-55 (2010)). Following functionalization, hydrophobic tails will be conjugated to the GAG (e.g., dermatan sulfate), then either peptide ligands, or a combination of selectin and ICAM-binding peptides will be conjugated to the GAG (e.g., dermatan sulfate) as described above. The tails will force the EC-SEAL-Alkyl Tail into micelles in aqueous environments. Mixed micelles can also be formulated and employed that include the DS-SILY conjugates described in US 2013/0190246 combined with one or more types of the EC-SEAL conjugates described herein. The DS-SILY and EC-SEAL conjugates can both have alkyl tails. By combining 1:1 DS-SILY-tail:EC-SEAL-tail mixed micelles are generated that will bind to endothelium, or to exposed ICAM, VCAM, selectin, and/or collagen. The release of DS-SILY-tail and EC-SEAL-tail molecules can coat any newly exposed collagen or activated endothelial cells over a 48-hour period after delivery. The alkyl tail structures can be optimized for micelle formation and for dissociation of the micelles over time.

Hydrophobication of the amine modified dermatan sulfate will be achieved by utilizing glycidyl ether conjugates of alkyl chains, such as isopropyl (C3), butyl (C4), hexyl (C6), octyl (C8), decyl (C10), or dodecyl (C12) glycidyl ether. The reaction between the glycidyl ether and the amine occurs preferentially over other available nucleophiles such as water or hydroxyl units (Shechter et al., Industrial & Engineering Chemistry 48:94-7 (1956)). The relative hydrophobicity of the resultant alkyl DS can be controlled by selecting the correct alkyl tail length ranging from C3 to C12. The reaction between DS-amine and the alkyl glycidyl ether will be achieved as follows. DS (1.0 g) will be dispersed in 70 mL of isopropanol with stirring. Subsequently a predetermined molar quantity of alkyl glycidyl ether will be added to the mixture and reacted for 3 h at 63° C. The resultant alkylated DS will be collected by filtration and washed with toluene to remove excess unreacted alkyl glycidyl ether. The alkylated DS will be lyophilized to obtain the dry material. This method has been used successfully to synthesize chitosan alkylate which, upon subsequent sulfonation, formed micelles capable of aiding the solubility of poorly soluble rotenone (Lao et al., Carbohydrate Polymers 82:1136-42 (2010)).

Micelle Characterization: CMC/Diameter/Zeta Potential: The critical micelle concentration (CMC) of the alkylated-DS will be measured using a zetasizer. In contrast to concentrations above the CMC, at the concentration below CMC, the intensity of the scattered light is not significantly different from that of water. In addition, the autocorrelation functions obtained show poor signal to noise ratios and no size distribution information is obtained (see website at quimica.udea.edu.co/~coloides/Anexol.pdf). 2006 (2006)). The micelle size and zeta potential will also be characterized at varying conditions, with and without the presence of serum proteins to study the impact of and interactions with proteins (Takeuchi K-I et al., FEBS letters 397:207-9 (1996)).

Micelle Dissociation: Fluorescence (monitoring emission spectrum at various wavelengths using an M5 plate reader) will be used for measuring micelle dissociation using pyrene which displays different fluorescence spectrum depending on the hydrophobicity of the environment (Wilhelm et al., Macromolecules 24:1033-40 (1991)). This technique will allow us to measure dissociation of the micelles on endothelial cell surfaces in the presence of serum and whole blood by measuring the change in pyrene fluorescence. Importantly, the EC-SEAL can be labeled with biotin for detection on collagen endothelial cells surfaces. This will allow verification that EC-SEAL conjugates bind to their targets as the micelles dissociate.

Micelle Dissociation and Binding to Collagen and Activated Endothelial Cells: The inventor has previously used ibidi Flow kits (Martinsried, Germany) to assess cell binding to collagen surfaces (Paderi et al., Biomaterials 32:2516-23 (2011)). A similar procedure will be used to assess micelle binding, and to assess micelle dissociation, and DS-SILY-tail and EC-SEAL-tail binding to collagen and activated endothelial cells upon micelle dissociation under flow. Briefly, each channel will be coated with fibrillar collagen, or with fibrillar collagen and patches of activated endothelial cells. Excess collagen and unbound endothelial cells will be removed from the flow channel by extensive rinsing with PBS through the channel. Micelles will be incubated in the channel at a concentration of 2 mM for 15 min at 37° C., and unbound micelles rinsed with PBS. Control channels will consist of collagen and endothelial cells not treated with micelles. Whole blood will be pushed through the flow channels by a syringe pump at a flow rate of 5.6 mL/h, corresponding to a physiologically relevant shear rate of 1000 s$^{-1}$ (Badimon et al., Circulation 78:1431-42 (1988)). For short-term experiments, after 5 min of flow, PBS pH 7.4 was pushed through at the same flow rate for 10 min to wash unbound cells. For long-term experiments, after exposure to flow for 5 minutes, blood will be exchanged for complete medium and cells will be returned to the incubator for 24 hours then again exposed to flow for 5 minutes, imaged and returned to the incubator for an additional 24 hours. They will then be exposed to flow again for 5 minutes, and imaged a final time. Brightfield and fluorescent images will be taken of each flow channel with a 10× objective. Images will be thresholded and quantified for micelle coverage, cellular coverage, and with the added step of application of avidin-Cy5 imaged for DS-SILY-tail or EC-SEAL-tail coverage, using ImageJ (NIH, Bethesda, Md.) and MatLab (Mathworks, Natick, Mass.) respectively.

Once optimal formulations have been determined (form micelles, dissociate over ~48 hours, bind to collagen and activated endothelial cells) we will further challenge the system by evaluating micelle binding when delivery formations contain both micelles and free DS-SILY and free EC-SEAL to ensure that binding of the micelles occurs in the presence of free DS-SILY and EC-SEAL. Since the micelles have a greater number of binding peptides per unit, there is no reason to think that the micelles will not efficiently compete with the free molecules for binding. However, ratios of 50:50, 75:25 and 90:10 free molecule:micelle will be evaluated in the flow system described in the previous paragraph to determine ratios that support efficient binding of both free molecule and micelles.

The ratio that best supports binding of free molecules and micelles will be challenged at 30 minutes, 24 hours and 48 hours with whole blood to assess platelet binding as we have done for the DS-SILY molecule (Paderi et al., Biomaterials 32:2516-23 (2011)). This ratio will also be assessed in HUVEC and leukocyte cell line HL60 co-culture model where HUVECS are challenged with TNFα, treated with the optimal ratio, challenged with HL60 and evaluated for DS-SILY/EC-SEAL coating, HL60 binding, and cytokine production.

At the completion of such procedures the DS-SILY and EC-SEAL tail size is appropriately tuned to induce micelle formation and allow for dissociation over a 48-hour period. We will also have evaluated the ability of DS-SILY and EC-SEAL to bind to collagen and activated endothelial cells respectively following dissociation from the micelles. Based on this we can further tune the number of selectin and ICAM peptides conjugated to the DS-SILY-tail and EC-SEAL-tail used to form micelles to optimize the probability of binding to newly exposed collagen and activated endothelial cells.

Alternative Approaches: If alkylation occurs at locations other than the reducing end, we will first acetylate all amines prior to creating a new amine at the reducing end. This will be done by dissolving 1 g of DS in 10 mL of formamide at room temperature and adding predetermined molar quantities of pyridine and acetic anhydride. The reaction mixture will be stirred for 12 hours prior to dialysis (MWCO 3,500 Da) for 3 days against distilled water and lyophilization. This has been successfully applied to similar chondroitin sulfate to achieve acetylation of the chondroitin sulfate (Li & Na, Biomacromolecules 12:1724-30 (2011)). These reactions have proven to be effective in adding alkyl chains to DS in a controlled fashion, leading to self-aggregation to micelles and nanoparticles.

An alternative coupling chemistry can be used if necessary. As amines are susceptible to reactions via carbodiimide chemistry, fatty acids may be directly reacted with the DS-amine utilizing 1-ethyl-3-(3-dimethylaminopropyl)-carbodiimide (EDC) as an intermediate. To achieve this reaction DS-amine (1 g) will be dissolved in a moderately acidic aqueous solution (~100 ml, pH 5-6) and diluted with 85 mL of methanol. The fatty-acid of choice will be added to the DS solution at a predetermined molar ratio followed by dropwise addition of EDC methanol solution (1:1 mole EDC:fatty acid) while stirring at room temperature. After for 24 h the reaction will be poured into excess methanol to precipitate. The precipitated material will be washed with methanol, and ether, successively, and then lyophilized. Previously, linoleic acid (LA) has been conjugated to chitosan by this method in order to achieve self-aggregating LA-Chitosan nanoparticles, which spontaneously formed into nanoparticles with a size range between 200-600 nm upon the addition of 1M NaCl solution (Chen et al., J. Agricult. & Food Chem. 51:3135-9 (2003)).

Additional characterization techniques, including field emission scanning electron microscopy of micelles on collagen, selectin, ICAM, and/or VCAM surfaces can be used in the event that zeta sizing, confocal microscopy, and ELISA are insufficient to characterize the interactions. In the event that pyrene is not sufficiently sensitive to allow for monitoring of micelle dissociation, fluorescently conjugated polysaccharide nanoparticles which have previously been used to assay cell-polysaccharide interactions, can be used (Huang et al., Pharmaceutical research 19:1488-94 (2002). This will be accomplished by conjugating a fluorophore directly to the alkylated-dermatan sulfate. A wide variety of fluorescent dyes can be conjugated to the dermatan sulfate including near-infrared dyes that would potentially allow for in-vivo imaging (Leevy et al., Bioconjugate chemistry 19:686-92 (2008)).

REFERENCES

1. Allon M. Current management of vascular access. Clin J Am Soc Nephrol 2007; 2:786-800.
2. Roy-Chaudhury P, Lee, T. Vascular Stenosis: Biology and Interventions. Current Opinion in Nephrology and Hypertension 2007; 16:516-22.
3. Roy-Chaudhury P, Kelly B S, Melhem M, et al. Vascular access in hemodialysis: issues, management, and emerging concepts. Cardiol Clin 2005; 23:249-73.
4. Roy-Chaudhury P, Sukhatme V P, Cheung A K. Hemodialysis Vascular Access Dysfunction: A Cellular and Molecular Viewpoint. Journal of the American Society of Nephrology 2006; 17:1112-27.
5. Pisoni R L, Arrington C J, Albert J M, et al. Facility hemodialysis vascular access use and mortality in countries participating in DOPPS: an instrumental variable analysis. Am J Kidney Dis 2009; 53:475-91.
6. Lee T, Chauhan V, Krishnamoorthy M, et al. Severe venous neointimal hyperplasia prior to dialysis access surgery. Nephrology, dialysis, transplantation: official publication of the European Dialysis and Transplant Association—European Renal Association 2011; 26:2264-70.
7. Chang C J, Ko P J, Hsu L A, et al. Highly increased cell proliferation activity in the restenotic hemodialysis vascular access after percutaneous transluminal angioplasty: implication in prevention of restenosis. Am J Kidney Dis 2004; 43:74-84.

8. Roy-Chaudhury P, Khan R, Campos B, et al. Pathogenetic role for early focal macrophage infiltration in a pig model of arteriovenous fistula (AVF) stenosis. The journal of vascular access 2013; 0:0.

9. Rajabi-Jagahrgh E, Krishnamoorthy M K, Roy-Chaudhury P, et al. Longitudinal Assessment of Hemodynamic Endpoints in Predicting Arteriovenous Fistula Maturation. Seminars in dialysis 2012.

10. Krishnamoorthy M K, Banerjee R K, Wang Y, Choe A K, Rigger D, Roy-Chaudhury P. Anatomic configuration affects the flow rate and diameter of porcine arteriovenous fistulae. Kidney Int 2012; 81:745-50.

11. Lee T, Roy-Chaudhury P. Advances and new frontiers in the pathophysiology of venous neointimal hyperplasia and dialysis access stenosis. Adv Chronic Kidney Dis 2009; 16:329-38.

12. Krishnamoorthy M K, Banerjee R K, Wang Y, et al. Hemodynamic wall shear stress profiles influence the magnitude and pattern of stenosis in a pig AV fistula. Kidney Int 2008; 74:1410-9.

13. Badimon L, Badimon J J, Turitto V T, Vallabhajosula S, Fuster V. Platelet thrombus formation on collagen type I. A model of deep vessel injury. Influence of blood rheology, von Willebrand factor, and blood coagulation. Circulation 1988; 78:1431-42.

14. Kim M C, Nam J H, Lee C S. Near-wall deposition probability of blood elements as a new hemodynamic wall parameter. Ann Biomed Eng 2006; 34:958-70.

15. Wu M H, Kouchi Y, Onuki Y, et al. Effect of differential shear stress on platelet aggregation, surface thrombosis, and endothelialization of bilateral carotid-femoral grafts in the dog. Journal of vascular surgery 1995; 22:382-90; discussion 90-2.

16. Liani M, Salvati F, Tresca E, et al. Arteriovenous fistula obstruction and expression of platelet receptors for von Willebrand factor and for fibrinogen (glycoproteins GPib and GPiib/iiia) in hemodialysis patients. The International journal of artificial organs 1996; 19:451-4.

17. Chuang Y C, Chen J B, Yang L C, Kuo C Y. Significance of platelet activation in vascular access survival of haemodialysis patients. Nephrology, dialysis, transplantation: official publication of the European Dialysis and Transplant Association—European Renal Association 2003; 18:947-54.

18. Roy-Chaudhury P, Y Wang, M Krishnamoorthy, J Zhang, R Banerjee, R Munda, S C Heffelfinger, L Arend Cellular Phenotypes in Hemodialysis Vascular Access Dysfunction. Nephrology, Dialysis and Transplantation 2007 In Revision.

19. Roy-Chaudhury P, Kelly B S, Miller M A, et al. Venous neointimal hyperplasia in polytetrafluoroethylene dialysis grafts. Kidney Int 2001; 59:2325-34.

20. Oberleithner H. Vascular endothelium leaves fingerprints on the surface of erythrocytes. Pflugers Archiv: European journal of physiology 2013; 465:1451-8.

21. Vlahu C A, Lemkes B A, Struijk D G, Koopman M G, Krediet R T, Vink H. Damage of the endothelial glycocalyx in dialysis patients. Journal of the American Society of Nephrology: JASN 2012; 23:1900-8.

22. Briet M, Burns K D. Chronic kidney disease and vascular remodeling: molecular mechanisms and clinical implications. Clin Sci (Lond) 2012; 123:399-416.

23. Stinghen A E, Pecoits-Filho R. Vascular damage in kidney disease: beyond hypertension. International journal of hypertension 2011; 2011:232683.

24. Brunet P, Gondouin B, Duval-Sabatier A, et al. Does uremia cause vascular dysfunction? Kidney & blood pressure research 2011; 34:284-90.

25. Wu C C, Wen S C, Yang C W, Pu S Y, Tsai K C, Chen J W. Plasma ADMA predicts restenosis of arteriovenous fistula. J Am Soc Nephrol 2009; 20:213-22.

26. Himmelfarb J, Hakim R M. Oxidative stress in uremia. Curr Opin Nephrol Hypertens 2003; 12:593-8.

27. Morris S T, Jardine A G. The vascular endothelium in chronic renal failure. J Nephrol 2000; 13:96-105.

28. Verbeke F H, Pannier B, Guerin A P, Boutouyrie P, Laurent S, London G M. Flow-mediated vasodilation in end-stage renal disease. Clin J Am Soc Nephrol; 6:2009-15.

29. Reitsma S, Slaaf D W, Vink H, van Zandvoort M A, oude Egbrink M G. The endothelial glycocalyx: composition, functions, and visualization. Pflügers Archiv-European Journal of Physiology 2007; 454:345-59.

30. Schouten M, Wiersinga W J, Levi M, van der Poll T. Inflammation, endothelium, and coagulation in sepsis. Journal of leukocyte biology 2008; 83:536-45.

31. van den Berg B M, Nieuwdorp M, Stroes E, Vink H. Glycocalyx and endothelial (dys) function: from mice to men. Pharmacol Rep 2006; 58:75-80.

32. Paderi J E, Stuart K, Sturek M, Park K, Panitch A. The inhibition of platelet adhesion and activation on collagen during balloon angioplasty by collagen-binding peptidoglycans. Biomaterials 2011; 32:2516-23.

33. Haverslag R, Pasterkamp G, Hoefer I E. Targeting Adhesion Molecules in Cardiovascular Disorders. Cardiovascular & Haematological Disorders—Drug Targets 2008; 8:252-60.

34. Ait-Oufella H, Maury E, Lehoux S, Guidet B, Offenstadt G. The endothelium: physiological functions and role in microcirculatory failure during severe sepsis. Applied Physiology in Intensive Care Medicine 2: Springer; 2012: 237-49.

35. Wong C-Y, de Vries M R, Wang Y, et al. Vascular remodeling and intimal hyperplasia in a novel murine model of arteriovenous fistula failure. Journal of Vascular Surgery 2014; 59:192-201.e1.

36. Karagkiozaki V. Nanomedicine highlights in atherosclerosis. Journal of Nanoparticle Research 2013; 15:1-17.

37. Lewis D R, Kamisoglu K, York A W, Moghe P V. Polymer-based therapeutics: nanoassemblies and nanoparticles for management of atherosclerosis. Wiley Interdisciplinary Reviews: Nanomedicine and Nanobiotechnology 2011; 3:400-20.

38. Wang Y, Krishnamoorthy M, Banerjee R, et al. Venous stenosis in a pig arteriovenous fistula model—anatomy, mechanisms and cellular phenotypes. Nephrol Dial Transplant 2008; 23:525-33.

39. Weinhart M, Groger D, Enders S, Dernedde J, Haag R. Synthesis of Dendritic Polyglycerol Anions and Their Efficiency Toward L-Selectin Inhibition. Biomacromolecules 2011; 12:2502-11.

40. Nishida Y, Uzawa H, Toba T, Sasaki K, Kondo H, Kobayashi K. A facile synthetic approach to L- and P-selectin blockers via copolymerization of vinyl monomers constructing the key carbohydrate modules of sialyl LewisX mimics. Biomacromolecules 2000; 1:68-74.

41. Butterfield K C, Caplan M, Panitch A. Identification and sequence composition characterization of chondroitin sulfate-binding peptides through peptide array screening. Biochemistry 2010; 49:1549-55.

42. Ferrante E A, Pickard J E, Rychak J, Klibanov A, Ley K. Dual targeting improves microbubble contrast agent adhesion to VCAM-1 and P-selectin under flow. Journal of Controlled Release 2009; 140:100-7.

43. Kalstad M M, Panitch A, Ehteshami G R, Massia S P. Inhibition of ICAM-mediated monocyte adhesion with a bioresponsive dextran-based conjugate. Engineering in Medicine and Biology, 2002 24th Annual Conference and the Annual Fall Meeting of the Biomedical Engineering Society EMBS/BMES Conference, 2002 Proceedings of the Second Joint; 2002 2002. p. 736-7 vol. 1.

44. Fukuda M N, Ohyama C, Lowitz K, et al. A peptide mimic of E-selectin ligand inhibits sialyl Lewis X-dependent lung colonization of tumor cells. Cancer Res 2000; 60:450-6.

45. Martens C L, Cwirla S E, Lee R Y, et al. Peptides which bind to E-selectin and block neutrophil adhesion. J Biol Chem 1995; 270:21129-36.

46. Scott R A, Paderi J E, Sturek M, Panitch A. Decorin mimic inhibits vascular smooth muscle proliferation and migration. PloS one 2013; 8:e82456.

47. Stenvinkel P, Ekstrom T J. Does the uremic milieu affect the epigenotype? J Ren Nutr 2009; 19:82-5.

48. Himmelfarb J. Uremic toxicity, oxidative stress, and hemodialysis as renal replacement therapy. Seminars in dialysis 2009; 22:636-43.

49. Vaziri N D. Oxidative stress in uremia: nature, mechanisms, and potential consequences. Semin Nephrol 2004; 24:469-73.

50. Himmelfarb J, Stenvinkel P, Ikizler T A, Hakim R M. The elephant in uremia: oxidant stress as a unifying concept of cardiovascular disease in uremia. Kidney Int 2002; 62:1524-38.

51. Serradell M, Diaz-Ricart M, Cases A, et al. Uremic medium causes expression, redistribution and shedding of adhesion molecules in cultured endothelial cells. Haematologica 2002; 87:1053-61.

52. Caballo C, Palomo M, Cases A, et al. NFkappaB in the development of endothelial activation and damage in uremia: an in vitro approach. PloS one 2012; 7:e43374.

53. Li F, Na K. Self-assembled chlorin e6 conjugated chondroitin sulfate nanodrug for photodynamic therapy. Biomacromolecules 2011; 12:1724-30.

54. Chen X-G, Lee C M, Park H-J. O/W emulsification for the self-aggregation and nanoparticle formation of linoleic acid modified chitosan in the aqueous system. Journal of agricultural and food chemistry 2003; 51:3135-9.

55. Leevy W M, Gammon S T, Johnson J R, et al. Noninvasive optical imaging of *staphylococcus aureus* bacterial infection in living mice using a Bis-dipicolylamine-Zinc (II) affinity group conjugated to a near-infrared fluorophore. Bioconjugate chemistry 2008; 19:686-92.

56. Rafat M, Rotenstein L S, Hu J L, Auguste D T. Engineered endothelial cell adhesion via VCAM1 and E-selectin antibody-presenting alginate hydrogels. Acta Biomaterialia 2012; 8:2697-703.

57. Feng Y, Chung D, Garrard L, et al. Peptides derived from the complementarity-determining regions of anti-Mac-1 antibodies block intercellular adhesion molecule-1 interaction with Mac-1. Journal of Biological Chemistry 1998; 273:5625-30.

58. Yusuf-Makagiansar H, Yakovleva T V, Tejo B A, et al. Sequence Recognition of α-LFA-1-derived Peptides by ICAM-1 Cell Receptors: Inhibitors of T-cell Adhesion. Chemical Biology & Drug Design 2007; 70:237-46.

59. Sakhalkar H S, Dalal M K, Salem A K, et al. Leukocyte-inspired biodegradable particles that selectively and avidly adhere to inflamed endothelium in vitro and in vivo. Proceedings of the National Academy of Sciences 2003; 100:15895-900.

60. Shechter L, Wynstra J, Kurkjy R P. Glycidyl ether reactions with amines. Industrial & Engineering Chemistry 1956; 48:94-7.

61. Lao S-B, Zhang Z-X, Xu H-H, Jiang G-B. Novel amphiphilic chitosan derivatives: Synthesis, characterization and micellar solubilization of rotenone. Carbohydrate Polymers 2010; 82:1136-42.

62. Application Note Surfactant micelle characterization using dynamic light scattering (see website at quimica.udea.edu.co/~coloides/Anexol.pdf). 2006.

63. Takeuchi K-i, Ishihara M, Kawaura C, Noji M, Furuno T, Nakanishi M. Effect of zeta potential of cationic liposomes containing cationic cholesterol derivatives on gene transfection. FEBS letters 1996; 397:207-9.

64. Wilhelm M, Zhao C L, Wang Y, et al. Poly (styrene-ethylene oxide) block copolymer micelle formation in water: a fluorescence probe study. Macromolecules 1991; 24:1033-40.

65. Huang M, Ma Z, Khor E, Lim L-Y. Uptake of FITC-chitosan nanoparticles by A549 cells. Pharmaceutical research 2002; 19:1488-94.

All patents and publications referenced or mentioned herein are indicative of the levels of skill of those skilled in the art to which the disclosure pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential.

The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a promoter" includes a plurality of such nucleic acids or promoters (for example, a solution of nucleic acids or a series of promoters), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The following statements of the invention are intended to describe and summarize various embodiments of the invention according to the foregoing description in the specification.

What is claimed:

1. A peptide conjugate comprising a glycosaminoglycan and from about 3 to about 50 peptide ligands covalently bonded to the glycosaminoglycan via a N-[β-maleimidopropionic acid]hydrazide (BMPH) linker, and wherein the peptide ligands bind to selectin, ICAM and/or VCAM, and wherein the peptide ligand comprises an amino acid sequence selected from:
   i) IDLMQARGC (SEQ ID NO: 107); IELLQARGC (SEQ ID NO: 108); QITWAQLWMMKGC (SEQ ID NO: 109); DGEATDGC (SEQ ID NO: 110); and ITDGEAGC (SEQ ID NO: 114); or
   ii) an amino acid sequence with at least about 90% sequence identity to an amino acid sequence of i).

2. The peptide conjugate of claim 1, further comprising a ($C_{2-18}$) alkyl tail bound to the glycosaminoglycan.

3. The peptide conjugate of claim 1, comprising from about 5 to about 40 peptide ligands capable of binding to selectin.

4. The peptide conjugate of claim 1, comprising from about 5 to about 40 peptide ligands capable of binding to ICAM and/or VCAM.

5. The peptide conjugate of claim 1, comprising from about 5 to about 20 peptide ligands capable of binding to a selectin and from about 5 to about 20 peptide ligands capable of binding to ICAM and/or VCAM.

6. The peptide conjugate of claim 1, comprising dermatan sulfate or chondroitin sulfate and from about 3 to about 25 peptide ligands, wherein the peptide ligands bind to selectin, ICAM and/or VCAM.

7. A peptide conjugate comprising dermatan sulfate and about 10, about 15, about 20 or about 30 peptide ligands, wherein the peptide ligands bind to selectin, ICAM and/or VCAM.

8. The peptide conjugate of claim 1, comprising dermatan sulfate and about 10 peptide ligands capable of binding to a selectin and about 10 peptide ligands capable of binding to ICAM and/or VCAM.

9. A method for treating a patient suffering from a disease associated with endothelial dysfunction, the method comprising administering to the patient a pharmaceutical composition comprising an effective amount of the peptide conjugate of claim 1.

10. The method of claim 9, wherein the disease associated with endothelial dysfunction is selected from the group consisting of atherosclerosis, coronary artery disease, diabetes mellitus, hypertension, hypercholesterolemia, rheumatoid arthritis, systemic lupus erythematosus, glaucoma, uremia, sepsis, and organ failure.

11. The method of claim 9, wherein the administration is intravenous, intraperitoneal, topical or through an implanted device.

12. The method of claim 9, wherein the patient is not undergoing or recovering from a vascular intervention procedure.

13. The method of claim 12, wherein the vascular intervention procedure comprises a percutaneous coronary intervention (PCI) procedure.

14. The method of claim 12, wherein the vascular intervention procedure comprising denuding a blood vessel.

15. The method of claim 9, wherein the endothelial dysfunction is characterized by permeated endothelial lining or damaged endothelial cells.

16. The method of claim 9, wherein the endothelial dysfunction is characterized by loss of glycocalyx.

17. The method of claim 9, wherein the endothelial dysfunction is characterized by a selectin protein expressed on the surface of endothelial cells and exposed to circulation.

18. The method of claim 9, wherein the endothelial dysfunction is at a site suffering from inflammation.

19. The method of claim 9, wherein the peptide conjugate is administered to achieve a plasma concentration of peptide ligand from 20 µM to 1000 µM proximate to dysfunctional endothelium.

20. The method of claim 19, wherein the peptide conjugate is administered to achieve a plasma concentration of peptide ligand from 100 µM to 400 µM proximate to dysfunctional endothelium.

21. A method for reducing inflammation at a vascular site in a patient, wherein the site (a) comprises permeated endothelial lining or damaged endothelial cells, and (b) is not undergoing or recovering from a vascular intervention procedure, the method comprising administering to the patient a pharmaceutical composition comprising an effective amount of the peptide conjugate of claim 1.

22. The method of claim 21, wherein the vascular intervention procedure comprises a percutaneous coronary intervention (PCI) procedure.

23. A peptide conjugate comprising a peptide ligand, a glycosaminoglycan, and from 1 to 3 optional alkyl tail(s), wherein the peptide ligand has a sequence selected from the group of IDLMQARGC (SEQ ID NO: 107); IELLQARGC (SEQ ID NO: 108); QITWAQLWMMKGC (SEQ ID NO: 109); DGEATDGC (SEQ ID NO: 110); and ITDGEAGC (SEQ ID NO: 114).

24. A composition comprising the peptide conjugate of claim 23.

25. A method comprising contacting one or more endothelial cells with the peptide conjugate of claim 23.

26. The peptide conjugate of claim 1, wherein the glycosaminoglycan is dextran, dextran sulfate, chondroitin, chondroitin sulfate, dermatan, dermatan sulfate, heparan sulfate, heparin, keratin, keratan sulfate, or hyaluronic acid.

* * * * *